(12) United States Patent
Kaula et al.

(10) Patent No.: US 10,347,381 B2
(45) Date of Patent: Jul. 9, 2019

(54) PROGRAMMING AND VIRTUAL REALITY REPRESENTATION OF STIMULATION PARAMETER GROUPS

(71) Applicant: Nuvectra Corporation, Plano, TX (US)

(72) Inventors: Norbert Kaula, Arvada, CO (US); Yohannes Iyassu, Denver, CO (US)

(73) Assignee: NUVECTRA CORPORATION, Plano, TX (US)

( * ) Notice: Subject to any disclaimer, the term of this patent is extended or adjusted under 35 U.S.C. 154(b) by 0 days.

(21) Appl. No.: 16/197,091

(22) Filed: Nov. 20, 2018

(65) Prior Publication Data

US 2019/0096530 A1 Mar. 28, 2019

Related U.S. Application Data

(60) Continuation of application No. 15/295,218, filed on Oct. 17, 2016, now Pat. No. 10,141,076, which is a
(Continued)

(51) Int. Cl.
*G16H 50/50* (2018.01)
*G06F 19/00* (2018.01)
(Continued)

(52) U.S. Cl.
CPC ........... *G16H 50/50* (2018.01); *A61N 1/0551* (2013.01); *A61N 1/3605* (2013.01);
(Continued)

(58) Field of Classification Search
CPC ...... G16H 50/50; G16H 40/63; A61N 1/0551; A61N 1/3605; A61N 1/36071; A61N 1/37247; G06F 19/00
See application file for complete search history.

(56) References Cited

U.S. PATENT DOCUMENTS 4,432,360 A 2/1984 Mumford et al.
5,286,202 A 2/1994 De Gyarfas et al.
(Continued)

FOREIGN PATENT DOCUMENTS

EP 1192972 4/2002
EP 2277586 1/2011
(Continued)

OTHER PUBLICATIONS

Synalink Features, SynaMed Web Page, http://synamed.com/synalinkFeatures.html., Copyright 2010, 2 pgs.
(Continued)

*Primary Examiner* — Catherine M Voorhees
*Assistant Examiner* — Roland Dinga
(74) *Attorney, Agent, or Firm* — Haynes and Boone, LLP; Eric Li

(57) ABSTRACT

The present disclosure involves a medical system that includes one or more implantable medical devices configured to deliver a medical therapy to a patient. The medical system also includes a portable electronic device on which a touch-sensitive user interface is implemented. The user interface is configured to provide a visual representation of the medical therapy through a hierarchy. The hierarchy includes a lower level representation of the medical therapy that corresponds to a stimulation program that includes a plurality of configurable stimulation parameters. The hierarchy includes a middle level representation of the medical therapy that corresponds to a stimulation program-set that includes a plurality of different stimulation programs. The hierarchy includes an upper level representation of the medical therapy that corresponds to a scrollable collection of stimulation program-sets that are represented by a plurality of digital cards, respectively.

20 Claims, 15 Drawing Sheets

Related U.S. Application Data division of application No. 13/601,631, filed on Aug. 31, 2012, now Pat. No. 9,471,753.

(51) Int. Cl.

| | |
|---|---|
| *G16H 40/63* | (2018.01) |
| *A61N 1/36* | (2006.01) |
| *A61N 1/372* | (2006.01) |
| *A61N 1/05* | (2006.01) |

(52) U.S. Cl.
CPC ..... *A61N 1/36071* (2013.01); *A61N 1/37247* (2013.01); *G06F 19/00* (2013.01); *G16H 40/63* (2018.01)

(56) References Cited

U.S. PATENT DOCUMENTS

| | | | |
|---|---|---|---|
| 5,304,206 A | 4/1994 | Baker, Jr. et al. | |
| 5,312,446 A | 5/1994 | Holschbach et al. | |
| 5,370,672 A | 12/1994 | Fowler et al. | |
| 5,383,914 A | 1/1995 | O'Phelan | |
| 5,421,830 A | 6/1995 | Epstein et al. | |
| 5,628,776 A | 5/1997 | Paul et al. | |
| 5,713,937 A | 2/1998 | Nappholz et al. | |
| 5,722,999 A | 3/1998 | Snell | |
| 5,724,985 A | 3/1998 | Snell et al. | |
| 5,724,996 A | 3/1998 | Piunti | |
| 5,819,740 A | 10/1998 | Muhlenberg | |
| 5,879,374 A | 3/1999 | Powers et al. | |
| 5,905,500 A | 5/1999 | Kamen et al. | |
| 5,938,690 A | 8/1999 | Law et al. | |
| 6,016,447 A | 1/2000 | Juran et al. | |
| 6,016,448 A | 1/2000 | Busacker et al. | |
| 6,052,624 A | 4/2000 | Mann | |
| 6,083,156 A | 7/2000 | Lisiecki | |
| 6,148,233 A | 11/2000 | Owen et al. | |
| 6,154,675 A | 11/2000 | Juran et al. | |
| 6,216,036 B1 | 4/2001 | Jenkins et al. | |
| 6,246,414 B1 | 6/2001 | Kawasaki | |
| 6,249,705 B1 | 6/2001 | Snell | |
| 6,278,890 B1 | 8/2001 | Chassaing et al. | |
| 6,307,554 B1 | 10/2001 | Arai et al. | |
| 6,308,102 B1 | 10/2001 | Sieracki et al. | |
| 6,345,200 B1 | 2/2002 | Mouchawar et al. | |
| 6,386,882 B1 | 5/2002 | Linberg | |
| 6,442,432 B2 | 8/2002 | Lee | |
| 6,525,727 B1 | 2/2003 | Junkins et al. | |
| 6,564,104 B2 | 5/2003 | Nelson et al. | |
| 6,587,104 B1 | 7/2003 | Hoppe | |
| 6,611,267 B2 | 8/2003 | Migdal et al. | |
| 6,622,048 B1 | 9/2003 | Mann et al. | |
| 6,669,631 B2 | 12/2003 | Norris et al. | |
| 6,786,405 B2 | 9/2004 | Weidenhoefer | |
| 6,852,080 B2 | 2/2005 | Bardy | |
| 6,882,982 B2 | 4/2005 | McMenimen et al. | |
| 6,895,280 B2 | 5/2005 | Meadows et al. | |
| 6,920,360 B2 | 7/2005 | Lee et al. | |
| 6,931,155 B1 | 8/2005 | Gioia | |
| 6,961,448 B2 | 11/2005 | Nichols et al. | |
| 6,961,617 B1 | 11/2005 | Snell | |
| 7,003,349 B1 | 2/2006 | Andersson et al. | |
| 7,034,823 B2 | 4/2006 | Dunnet | |
| 7,058,453 B2 | 6/2006 | Nelson et al. | |
| 7,060,030 B2 | 6/2006 | Von Arx et al. | |
| 7,065,409 B2 | 6/2006 | Mazar | |
| 7,066,910 B2 | 6/2006 | Bauhahn et al. | |
| 7,076,303 B2 | 7/2006 | Linberg | |
| 7,087,015 B1 | 8/2006 | Comrie et al. | |
| 7,092,761 B1 | 8/2006 | Cappa et al. | |
| 7,107,102 B2 | 9/2006 | Daignault et al. | |
| 7,142,923 B2 | 11/2006 | North et al. | |
| 7,181,286 B2 | 2/2007 | Sieracki et al. | |
| 7,181,505 B2 | 2/2007 | Haller et al. | |
| 7,184,837 B2 | 2/2007 | Goetz | |
| 7,239,926 B2 | 7/2007 | Goetz | |
| 7,266,412 B2 | 9/2007 | Stypulkowski | |
| 7,299,085 B2 | 11/2007 | Bergelson et al. | |
| 7,359,751 B1 | 4/2008 | Erickson et al. | |
| 7,373,204 B2 | 5/2008 | Gelfand et al. | |
| 7,440,806 B1 | 10/2008 | Whitehurst et al. | |
| 7,452,336 B2 | 11/2008 | Thompson | |
| 7,463,927 B1 | 12/2008 | Chaouat | |
| 7,474,223 B2 | 1/2009 | Nycz et al. | |
| 7,481,759 B2 | 1/2009 | Whitehurst et al. | |
| 7,489,970 B2 | 2/2009 | Lee et al. | |
| 7,496,403 B2 | 2/2009 | Cao et al. | |
| 7,499,048 B2 | 3/2009 | Sieracki et al. | |
| 7,505,815 B2 | 3/2009 | Lee et al. | |
| 7,551,960 B2 | 6/2009 | Forsberg et al. | |
| 7,602,384 B2 | 10/2009 | Rosenberg et al. | |
| 7,617,002 B2 | 11/2009 | Goetz | |
| 7,627,372 B2 | 12/2009 | Vaisnys et al. | |
| 7,640,059 B2 | 12/2009 | Forsberg et al. | |
| 7,657,317 B2 | 2/2010 | Thacker et al. | |
| 7,685,005 B2 | 3/2010 | Riff et al. | |
| 7,711,603 B2 | 5/2010 | Vanker et al. | |
| 7,720,549 B2 | 5/2010 | Schroeppel et al. | |
| 7,747,330 B2 | 6/2010 | Nolan et al. | |
| 7,774,067 B2 | 8/2010 | Keacher et al. | |
| 7,778,710 B2 | 8/2010 | Propato | |
| 7,801,596 B2 | 9/2010 | Fischell et al. | |
| 7,801,611 B2 | 9/2010 | Persen et al. | |
| 7,805,199 B2 | 9/2010 | KenKnight et al. | |
| 7,822,483 B2 | 10/2010 | Stone et al. | |
| 7,853,323 B2 | 12/2010 | Goetz | |
| 7,885,712 B2 | 2/2011 | Goetz et al. | |
| 7,890,180 B2 | 2/2011 | Quiles et al. | |
| 7,928,995 B2 | 4/2011 | Daignault | |
| 7,934,508 B2 | 5/2011 | Behm | |
| 7,940,933 B2 | 5/2011 | Corndorf | |
| 7,953,492 B2 | 5/2011 | Corndorf | |
| 7,953,612 B1 | 5/2011 | Palmese et al. | |
| 7,957,808 B2 | 6/2011 | Dawant et al. | |
| 7,978,062 B2 | 7/2011 | LaLonde et al. | |
| 7,991,482 B2 | 8/2011 | Bradley | |
| 8,014,863 B2 | 9/2011 | Zhang et al. | |
| 8,021,298 B2 | 9/2011 | Barid et al. | |
| 8,027,726 B2 | 9/2011 | Ternes | |
| 8,046,241 B1 | 10/2011 | Dodson | |
| 8,060,216 B2 | 11/2011 | Greenberg et al. | |
| 8,068,915 B2 | 11/2011 | Lee et al. | |
| 8,068,918 B2 | 11/2011 | Vallapureddy et al. | |
| 8,078,440 B2 | 12/2011 | Otto et al. | |
| 8,082,162 B2 | 12/2011 | Flood | |
| 8,121,702 B2 | 2/2012 | King | |
| 8,135,566 B2 | 3/2012 | Marshall et al. | |
| 8,140,160 B2 | 3/2012 | Pless et al. | |
| 8,140,167 B2 | 3/2012 | Donders et al. | |
| 8,160,328 B2 | 4/2012 | Goetz et al. | |
| 8,160,704 B2 | 4/2012 | Freeberg | |
| 8,165,385 B2 | 4/2012 | Reeves et al. | |
| 8,187,015 B2 | 5/2012 | Boyd et al. | |
| 8,200,324 B2 | 6/2012 | Shen et al. | |
| 8,200,340 B2 | 6/2012 | Skelton et al. | |
| 8,219,206 B2 | 7/2012 | Skelton et al. | |
| 8,233,991 B2 | 7/2012 | Woods et al. | |
| 8,246,680 B2 | 8/2012 | Betz et al. | |
| 8,249,713 B2 | 8/2012 | Fang et al. | |
| 8,255,060 B2 | 8/2012 | Goetz et al. | |
| 8,323,218 B2 | 12/2012 | Davis et al. | |
| 8,326,433 B2 | 12/2012 | Blum et al. | |
| 8,340,775 B1 | 12/2012 | Cullen et al. | |
| 8,382,666 B1 | 2/2013 | Mao et al. | |
| 8,386,032 B2 | 2/2013 | Bachinski et al. | |
| 8,401,666 B2 | 3/2013 | Skelton et al. | |
| 8,428,727 B2 | 4/2013 | Bolea et al. | |
| 9,375,582 B2 | 6/2016 | Kaula et al. | |
| 10,141,076 B2 * | 11/2018 | Kaula | A61N 1/0551 |
| 2001/0037220 A1 | 11/2001 | Merry et al. | |
| 2003/0076301 A1 | 4/2003 | Tsuk et al. | |
| 2003/0107572 A1 | 6/2003 | Smith et al. | |
| 2003/0139652 A1 | 7/2003 | Kang et al. | |
| 2003/0171911 A1 | 9/2003 | Fairweather | |
| 2003/0177031 A1 | 9/2003 | Malek | |

(56) References Cited

U.S. PATENT DOCUMENTS

| | | |
|---|---|---|
| 2004/0088374 A1 | 5/2004 | Webb et al. |
| 2004/0122477 A1 | 6/2004 | Whitehurst et al. |
| 2004/0210273 A1 | 10/2004 | Wang |
| 2005/0107831 A1 | 5/2005 | Hill et al. |
| 2005/0149356 A1 | 7/2005 | Cyr et al. |
| 2005/0168460 A1 | 8/2005 | Razdan et al. |
| 2005/0277872 A1 | 12/2005 | Colby et al. |
| 2006/0089888 A1 | 4/2006 | Roger |
| 2006/0100832 A1 | 5/2006 | Bowman |
| 2006/0241720 A1 | 10/2006 | Woods et al. |
| 2006/0242159 A1 | 10/2006 | Bishop et al. |
| 2006/0282168 A1 | 12/2006 | Sherman et al. |
| 2007/0078497 A1 | 4/2007 | Vandanacker |
| 2007/0093998 A1 | 4/2007 | El-Baroudi et al. |
| 2007/0179349 A1 | 8/2007 | Hoyme et al. |
| 2007/0203537 A1 | 8/2007 | Goetz et al. |
| 2007/0203538 A1 | 8/2007 | Stone et al. |
| 2007/0203543 A1 | 8/2007 | Stone et al. |
| 2007/0213790 A1 | 9/2007 | Nolan et al. |
| 2008/0004675 A1 | 1/2008 | King et al. |
| 2008/0033303 A1 | 2/2008 | Wariar et al. |
| 2008/0046036 A1 | 2/2008 | King et al. |
| 2008/0140161 A1 | 6/2008 | Goetz et al. |
| 2008/0177362 A1 | 7/2008 | Phillips et al. |
| 2008/0218517 A1 | 9/2008 | Holmdahl |
| 2008/0262565 A1 | 10/2008 | Bentwich |
| 2009/0018617 A1 | 1/2009 | Skelton et al. |
| 2009/0018619 A1 | 1/2009 | Skelton et al. |
| 2009/0024178 A1 | 1/2009 | Hennig |
| 2009/0048871 A1 | 2/2009 | Skomra |
| 2009/0089034 A1 | 4/2009 | Penney et al. |
| 2009/0099624 A1 | 4/2009 | Kokones et al. |
| 2009/0132009 A1 | 5/2009 | Torgenson et al. |
| 2009/0136094 A1 | 5/2009 | Driver et al. |
| 2009/0196471 A1 | 8/2009 | Goetz et al. |
| 2009/0234873 A1 | 9/2009 | Li et al. |
| 2009/0264967 A1 | 10/2009 | Giftakis et al. |
| 2009/0281596 A1 | 11/2009 | King et al. |
| 2010/0004033 A1 | 1/2010 | Choe et al. |
| 2010/0010566 A1 | 1/2010 | Thacker et al. |
| 2010/0010574 A1 | 1/2010 | Skelton et al. |
| 2010/0010580 A1 | 1/2010 | Skelton et al. |
| 2010/0058462 A1 | 3/2010 | Chow |
| 2010/0076534 A1 | 3/2010 | Mock |
| 2010/0090004 A1 | 4/2010 | Sands et al. |
| 2010/0106475 A1 | 4/2010 | Smith et al. |
| 2010/0123547 A1 | 5/2010 | Stevenson et al. |
| 2010/0152534 A1 | 6/2010 | Kim et al. |
| 2010/0161345 A1 | 6/2010 | Cain et al. |
| 2010/0198103 A1 | 8/2010 | Meadows et al. |
| 2010/0198304 A1 | 8/2010 | Wang |
| 2010/0222845 A1 | 9/2010 | Goetz |
| 2010/0223020 A1 | 9/2010 | Goetz |
| 2010/0265072 A1 | 10/2010 | Goetz et al. |
| 2010/0268304 A1 | 10/2010 | Matos |
| 2010/0280578 A1 | 11/2010 | Skelton et al. |
| 2011/0004059 A1 | 1/2011 | Arneson et al. |
| 2011/0015514 A1 | 1/2011 | Skalli et al. |
| 2011/0015693 A1 | 1/2011 | Williamson |
| 2011/0023343 A1 | 2/2011 | Turner et al. |
| 2011/0038498 A1 | 2/2011 | Edgar |
| 2011/0040546 A1 | 2/2011 | Gerber et al. |
| 2011/0040547 A1 | 2/2011 | Gerber et al. |
| 2011/0046697 A1 | 2/2011 | Gerber et al. |
| 2011/0054560 A1 | 3/2011 | Rosenberg et al. |
| 2011/0054870 A1 | 3/2011 | Dariush et al. |
| 2011/0077459 A1 | 3/2011 | Rofougaran |
| 2011/0077616 A1 | 3/2011 | Bennet et al. |
| 2011/0093030 A1 | 4/2011 | Goetz et al. |
| 2011/0093047 A1 | 4/2011 | Davis et al. |
| 2011/0093051 A1 | 4/2011 | Davis et al. |
| 2011/0153341 A1 | 6/2011 | Diaz-Cortes |
| 2011/0170739 A1 | 7/2011 | Gillam et al. |
| 2011/0172564 A1 | 7/2011 | Drew |
| 2011/0172737 A1 | 7/2011 | Davis et al. |
| 2011/0172744 A1 | 7/2011 | Davis et al. |
| 2011/0185178 A1 | 7/2011 | Gotthardt |
| 2011/0191275 A1 | 8/2011 | Lujan et al. |
| 2011/0224523 A1 | 9/2011 | Burdiman |
| 2011/0246219 A1 | 10/2011 | Smith et al. |
| 2011/0264165 A1 | 10/2011 | Molnar et al. |
| 2011/0270358 A1 | 11/2011 | Davis et al. |
| 2011/0282414 A1 | 11/2011 | Kothandaraman et al. |
| 2011/0305376 A1 | 12/2011 | Neff |
| 2011/0307284 A1 | 12/2011 | Thompson et al. |
| 2011/0313268 A1 | 12/2011 | Kokones et al. |
| 2011/0313487 A1 | 12/2011 | Kokones et al. |
| 2012/0041518 A1 | 2/2012 | Kim et al. |
| 2012/0046715 A1 | 2/2012 | Moffitt et al. |
| 2012/0071947 A1 | 3/2012 | Gupta et al. |
| 2012/0083857 A1 | 4/2012 | Bradley et al. |
| 2012/0084689 A1 | 4/2012 | Ledet et al. |
| 2012/0089008 A1 | 4/2012 | Strehl et al. |
| 2012/0109230 A1 | 5/2012 | Kothandaraman et al. |
| 2012/0192874 A1 | 8/2012 | Bolea et al. |
| 2012/0239116 A1 | 9/2012 | Lee et al. |
| 2012/0256857 A1 | 10/2012 | Mak |
| 2012/0265269 A1 | 10/2012 | Lui et al. |
| 2012/0277828 A1 | 11/2012 | O'Conner et al. |
| 2012/0290041 A1 | 11/2012 | Kim et al. |
| 2012/0290272 A1 | 11/2012 | Bryan |
| 2012/0290976 A1 | 11/2012 | Lahm et al. |
| 2012/0296392 A1 | 11/2012 | Lee et al. |
| 2012/0296396 A1 | 11/2012 | Moffitt et al. |
| 2012/0296397 A1 | 11/2012 | Vansickle |
| 2012/0303087 A1 | 11/2012 | Moffitt et al. |
| 2012/0310300 A1 | 12/2012 | Kaula et al. |
| 2013/0023950 A1 | 1/2013 | Gauthier |
| 2013/0060299 A1 | 3/2013 | Polefko et al. |
| 2013/0060300 A1 | 3/2013 | Polefko et al. |
| 2013/0060301 A1 | 3/2013 | Polefko et al. |
| 2013/0060302 A1 | 3/2013 | Polefko et al. |
| 2013/0079848 A1 | 3/2013 | Campbell et al. |

FOREIGN PATENT DOCUMENTS

| | | |
|---|---|---|
| WO | WO 9959106 | 11/1999 |
| WO | WO 2002009808 | 2/2002 |
| WO | WO 02084637 | 10/2002 |
| WO | WO 2009113102 | 9/2009 |
| WO | WO 2011028261 | 3/2011 |
| WO | WO 2011063248 | 5/2011 |
| WO | WO 2011104028 | 9/2011 |
| WO | WO 2011123669 | 10/2011 |
| WO | WO 2012018851 | 2/2012 |
| WO | WO 2012021862 | 2/2012 |
| WO | WO 2012135949 | 10/2012 |
| WO | WO 2013023085 | 2/2013 |

OTHER PUBLICATIONS

Boston Scientific Corporation, "Boston Scientific Precision Spectra System Programming Manual", Copyright 2010, 580 pgs.

Freescale Semiconductor, Inc., "i.MX51 Applications Processors for Consumer and Industrial Products," Data Sheet Technical Data, Document No. IMX51CEC, Rev. 4 (Aug. 2010) 200 pages.

\* cited by examiner

PROGRAMMING AND VIRTUAL REALITY REPRESENTATION OF STIMULATION PARAMETER GROUPS

PRIORITY DATA

This application is a continuation of U.S. patent application Ser. No. 15/295,218 filed Oct. 17, 2016, which is a divisional of Ser. No. 13/601,631, filed Aug. 31, 2012, now issued as U.S. Pat. No. 9,471,753, the disclosures of each of which are hereby incorporated by reference in their respective entireties as if fully set forth below and for all applicable purposes.

BACKGROUND

As medical device technologies continue to evolve, active implanted medical devices have gained increasing popularity in the medical field. For example, one type of implanted medical device includes neurostimulator devices, which are battery-powered or battery-less devices that are designed to deliver electrical stimulation to a patient. Through proper electrical stimulation, the neurostimulator devices can provide pain relief for patients.

An implanted medical device (for example a neurostimulator) can be controlled using an electronic programming device such as a clinician programmer or a patient programmer. These programmers can be used by medical personnel or the patient to define the particular electrical stimulation therapy to be delivered to a target area of the patient's body or alter one or more stimulation parameters of the electrical stimulation therapy. Advances in the medical device field have improved these electronic programmers. However, existing electronic programmers may still have shortcomings such as inadequate tracking and representation of stimulation therapies. For example, existing electronic programmers may not allow a user to track the stimulation parameters and their effects on the patient in a visual and intuitive manner.

Therefore, although electronic programming devices for controlling implanted medical devices have been generally adequate for their intended purposes, they have not been entirely satisfactory in every aspect.

SUMMARY

One aspect of the present disclosure involves electronic device configured to provide a visualization of stimulation parameters for an implantable medical device. The electronic device includes: a touchscreen configured to receive input from a user and display an output to the user; a memory storage component configured to store programming code; and a computer processor configured to execute the programming code to establish a graphical user interface via the touchscreen, wherein the graphical user interface is configured to visualize the stimulation parameters via the touchscreen and through a hierarchy of stimulation programs, stimulation program-sets, and a stimulation program-set list, wherein: the stimulation program-set list includes virtual representations of a plurality of the stimulation program-sets, wherein the virtual representation of each stimulation program-set contains respective stimulation information associated with the stimulation program-set; each stimulation program-set includes virtual representations of a plurality of the stimulation programs, wherein the virtual representation of each stimulation program contains respective stimulation parameters associated with the stimulation program; and each stimulation program includes a programming screen that displays a virtual representation of the implantable medical device and a plurality of virtual control mechanisms operable to configure the stimulation parameters of the stimulation program.

Another aspect of the present disclosure involves a medical system. The medical system includes: one or more implantable medical devices configured to deliver a medical therapy to a patient; and a portable electronic device on which a touch-sensitive user interface is implemented, wherein the user interface is configured to provide a visual representation of the medical therapy through a hierarchy that includes: a lower level representation of the medical therapy that corresponds to a stimulation program, wherein the stimulation program can run on the one or more implantable medical devices to cause the one or more implantable medical devices to stimulate a body tissue of the patient as part of the medical therapy, and wherein the stimulation program includes a plurality of configurable stimulation parameters; a middle level representation of the medical therapy that is at least one hierarchical level above the lower level representation of the medical therapy, wherein the middle level representation of the medical therapy corresponds to a stimulation program-set that includes a plurality of different stimulation programs; and an upper level representation of the medical therapy that is at least one hierarchical level above the middle level representation of the medical therapy, wherein the upper level representation of the medical therapy corresponds to a scrollable collection of stimulation program-sets, wherein the stimulation program-sets are represented by a plurality of digital cards, respectively.

Yet another aspect of the present disclosure involves a method of visualizing medical therapy associated with an implantable medical device. The method includes: providing a first level user interface for a stimulation program that can be executed on the implantable medical device to provide electrical stimulation for a patient as a part of the medical therapy, wherein the first level user interface is configured to display, and allow an adjustment of, a plurality of stimulation parameters of the stimulation program; providing a second level user interface for a stimulation program-set that is a collection of different stimulation programs, wherein the second level user interface is configured to display a plurality of visual abstractions that each correspond to a respective one of the stimulation programs, and wherein each visual abstraction of the stimulation program displays at least one of the stimulation parameters associated with the respective stimulation program; and providing a third level user interface for a stimulation program-set list that is a collection of different stimulation program-sets, wherein the third level user interface is configured to display a scrollable virtual carousel made up of a plurality of visual abstractions that each correspond to a respective one of the stimulation program-sets, and wherein each visual abstraction of the stimulation program-set displays at least one of: a patient-defined stimulation map and a patient-defined pain map.

One more aspect of the present disclosure involves an electronic apparatus for visually representing a stimulation therapy for a patient. The electronic apparatus includes: input/output means for communicating with a user, input/output means including a touch-sensitive screen configured to detect an input from the user and display an output to the user; memory storage means for storing executable instructions; and computer processor means for executing the instructions to perform: configuring a stimulation program in a first programming screen, the stimulation program including a plurality of stimulation parameters that are associated with a stimulation device capable of delivering the stimulation therapy to the patient; configuring a stimulation program-set in a second programming screen, the stimulation program-set including a plurality of the stimulation programs; and configuring a stimulation program-set list in a third programming screen, the stimulation program-set list including a plurality of the stimulation program-sets; wherein the first, second, and third programming screens are different from one another.

BRIEF DESCRIPTION OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In the figures, elements having the same designation have the same or similar functions.

DETAILED DESCRIPTION

Figure 1:
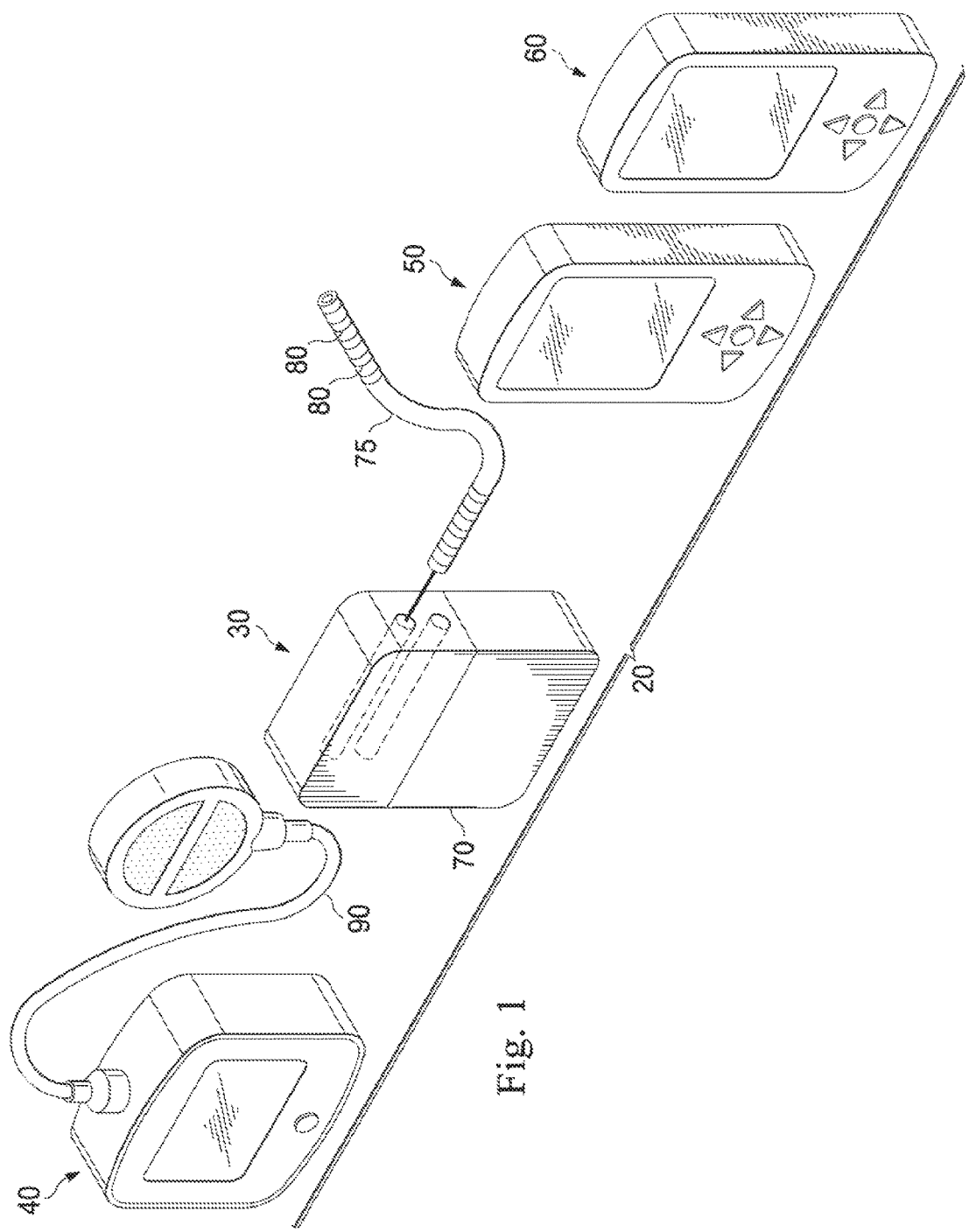
FIG. 1 is a simplified block diagram of a medical system according to various aspects of the present disclosure.

It is to be understood that the following disclosure provides many different embodiments, or examples, for implementing different features of the invention. Specific examples of components and arrangements are described below to simplify the present disclosure. These are, of course, merely examples and are not intended to be limiting. Various features may be arbitrarily drawn in different scales for simplicity and clarity.

Electronic programmers have been used to configure or program active implanted medical devices such as neurostimulators so that they can be operated in a certain manner. These electronic programmers include clinician programmers and patient programmers, each of which may be a handheld device. A clinician programmer allows a medical professional (e.g., a doctor or a nurse) to define the particular electrical stimulation therapy to be delivered to a target area of the patient's body, while a patient programmer allows a patient to alter one or more parameters of the electrical stimulation therapy.

Over the years, these electronic programmers have achieved significant improvements, for example, improvements in size, power consumption, lifetime, and ease of use. However, existing programmers in the medical field may still have drawbacks. One such drawback of existing programmers is their inability to provide adequate visual representation and tracking of the medical therapy delivered to the patient.

For example, electrical neural stimulation (a form of medical therapy) may include a plurality of stimulation parameters such as electrode polarity, frequency, pulse width, current amplitude, voltage amplitude, and whether a lead is active or inactive, and the orientation of the lead. Existing programmers lack functionality to visually represent groups of these stimulation parameters or multiple groups of these parameters in an intuitive and efficient manner. Often times, only one group of stimulation parameters is presented to the user, while the user has to develop mental images of other groups of stimulation parameters. In addition, existing programmers are incapable of associating customized pain maps or stimulation maps with their corresponding group of stimulation parameters. Furthermore, existing programmers are deficient with respect to providing management functionalities for the stimulation parameters. For example, management tasks such as naming a group of stimulation parameters, deleting a group of stimulation parameters, or locking a group of stimulation parameters (to prevent further modification) may be difficult to perform.

To overcome these problems associated with existing electronic programmers, a hierarchical visual user interface is implemented on an electronic programmer according to various aspects of the present disclosure. The hierarchical visual user interface provides an intuitive and efficient visual representation of the stimulation parameters. The hierarchical visual user interface also enables easy tracking of user-defined stimulation maps and pain maps in association with their respective groups of stimulation parameters. Various aspects of the electronic programmer and the hierarchical visual user interface implemented thereon are now described in more detail below.

Referring to FIG. 1, a simplified block diagram of an implanted medical device system 20 is illustrated to provide an example context of the various aspects of the present disclosure. The implanted medical system 20 includes an implantable medical device 30, an external charger 40, a patient programmer 50, and a clinician programmer 60. The implantable medical device 30 can be implanted in a patient's body tissue. In the illustrated embodiment, the implantable medical device 30 includes an implanted pulse generator (IPG) 70 that is coupled to one end of an implanted lead 75. The other end of the implanted lead 75 includes multiple electrode surfaces 80 through which electrical current is applied to a desired part of a body tissue of a patient. The implanted lead 75 incorporates electrical conductors to provide a path for that current to travel to the body tissue from the IPG 70. Although only one implanted lead 75 is shown in FIG. 1, it is understood that a plurality of implanted leads may be attached to the IPG 70.

Although an IPG is used here as an example, it is understood that the various aspects of the present disclosure apply to an external pulse generator (EPG) as well. An EPG is intended to be worn externally to the patient's body. The EPG connects to one end of one or more percutaneous, or skin-penetrating, leads. The other end of the percutaneous lead is implanted within the body and incorporates multiple electrode surfaces analogous in function and use to those of an implanted lead.

The external charger 40 of the medical device system 20 provides electrical power to the IPG 70. The electrical power may be delivered through a charging coil 90. The IPG 70 may also incorporate power-storage components such as a battery or capacitor so that it may be powered independently of the external charger 40 for a period of time, for example from a day to a month, depending on the power requirements of the therapeutic electrical stimulation delivered by the IPG.

The patient programmer 50 and the clinician programmer 60 may be portable handheld devices that can be used to configure the IPG 70 so that the IPG 70 can operate in a certain way. The patient programmer 50 is used by the patient in whom the IPG 70 is implanted. The patient may adjust the parameters of the stimulation, such as by selecting a program, changing its amplitude, frequency, and other parameters, and by turning stimulation on and off. The clinician programmer 60 is used by a medical personnel to configure the other system components and to adjust stimulation parameters that the patient is not permitted to control, such as by setting up stimulation programs among which the patient may choose, selecting the active set of electrode surfaces in a given program, and by setting upper and lower limits for the patient's adjustments of amplitude, frequency, and other parameters.

In the embodiments discussed below, the clinician programmer 60 is used as an example of the electronic programmer on which the hierarchical user interface (that provides a visual representation of stimulation parameters) can be displayed. However, it is understood that the hierarchical user interface according to the present disclosure may also be displayed on the patient programmer 50 or other touch screen programming devices (such as smart-phones or tablet computers) in other embodiments. Regardless of the programming device used, the hierarchical user interface may be accessible through a touch-sensitive screen.

FIGS. 2-10 are various program windows (also referred to as programming screens) showing different aspects of such hierarchical user interface 100 according to an embodiment. In more detail, referring to FIG. 2, the user interface 100 displays a program window 105A that illustrates how a group of stimulation parameters may be entered. The group of stimulation parameters may be referred to as a stimulation program, which corresponds to a lower level in the hierarchy of the user interface 100.

Figure 2:
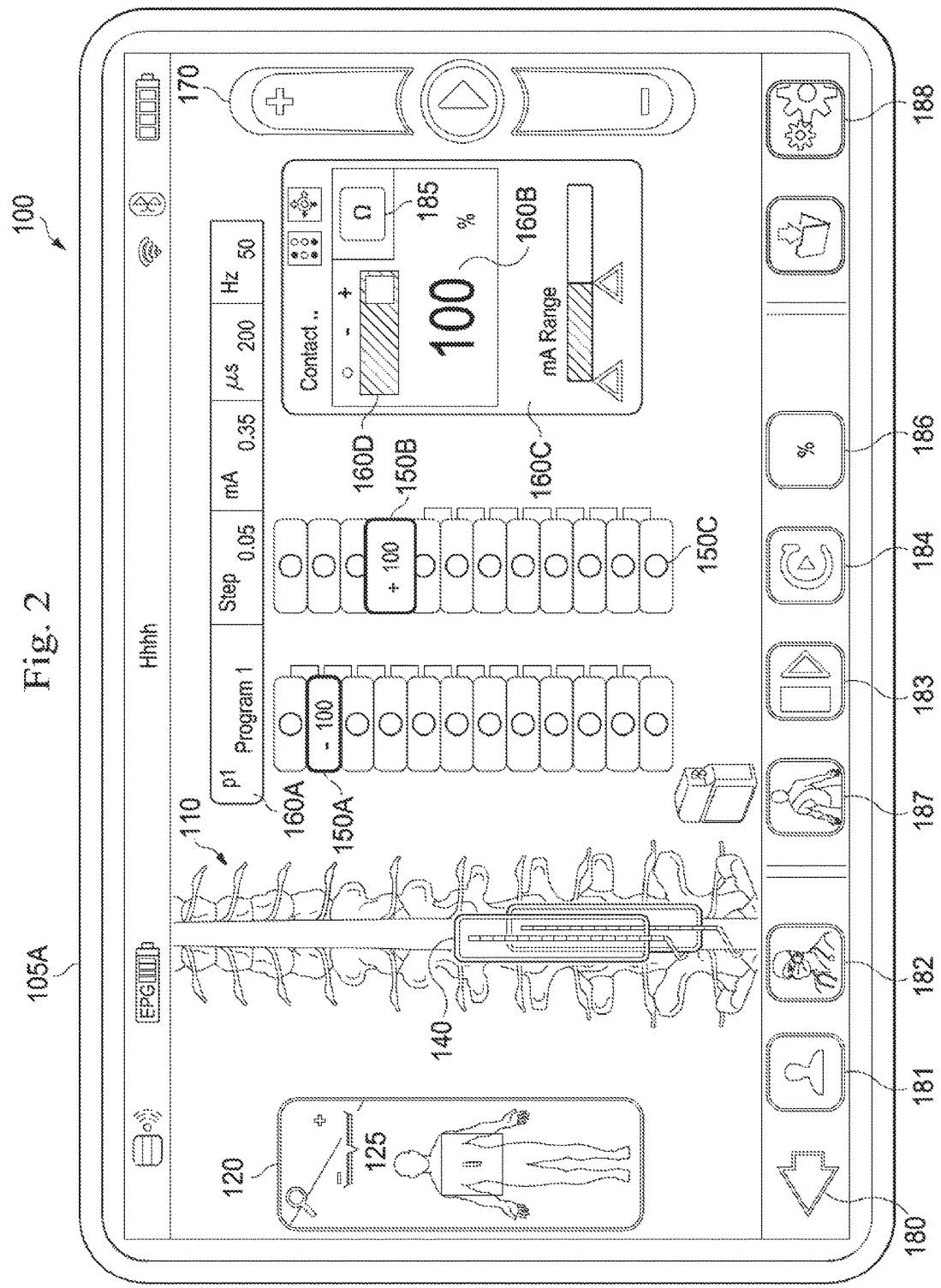
FIGS. 2-10 are various programming screens of a user interface for visualizing a medical therapy according to various aspects of the present disclosure.

As seen is FIG. 2, the program window 105A displays a virtual reality representation of an anatomical environment 110 (also referred to as anatomical surroundings) of a human body representing a patient. The virtual reality representation of the anatomical environment 110 may involve 3-D or 2-D models. In the embodiment shown in FIG. 2, the anatomical environment 110 includes a portion of a spine. In other embodiments, the anatomical environment 110 may include other parts of the human body, for example the brain, the heart, or the abdomen, etc.

In some embodiments, the patient's physiological data (for example the patient's height or weight) is obtained by detecting user input through the user interface 100. In other embodiments, the patient's physiological data may be obtained or through another suitable mechanism such as from an electronic database, which can be remote or local to the programmer. According to the various aspects of the present disclosure, the virtual reality representation of the anatomical environment 110 may be customized in response to the patient's physiological data. For example, the spine (or another implementation of the anatomical environment) may be scaled based on the height of the patient.

The program window 105A also includes a graphical display 120 that shows an entire human body (representing the patient's body). A portion of the human body corresponding to the anatomical environment 110 is highlighted by a box superimposed on the human body. The user can quickly access a particular location of the human body by moving the box to that location. As the box is being moved, the anatomical environment 110 is updated to reflect the change. The program window 105A also offers a zoom feature 125 that can be used to show a closer view (by zooming in) or a farther view (by zooming out) of the human body in the graphical display 120. In other words, when the zoom feature 125 is activated to zoom in the human body, a more detailed view (e.g., showing fewer vertebrae) of the anatomical environment 110 is shown. Conversely, when the zoom feature 125 is activated to zoom out of the human body, a less detailed view (e.g., showing more vertebrae) of the anatomical environment 110 is shown.

A user (for example a healthcare professional such as a physician) may choose to display a virtual reality representation of medical devices 140 near or at the anatomical environment 110. The selection and display of the virtual reality representation of medical devices are described in more detail in U.S. patent application Ser. No. 13/601,449, filed on Aug. 31, and entitled "VIRTUAL REALITY REPRESENTATION OF MEDICAL DEVICES", the content of which are herein incorporated by reference in its entirety.

In the embodiment shown in FIG. 2, the medical devices 140 are two "12 contact percutaneous" leads having a plurality of programmable electrodes 150. Each of the electrodes can be programmed as a cathode (such as electrode 150A), an anode (such as electrode 150B), or as an inactive electrode (such as electrode 150C). The program window 105A also includes a plurality of programming boxes) 160 that are used to display the current stimulation parameter settings for a selected electrode 150.

For example, the anode electrode 150B is the selected electrode in the example shown in FIG. 2. The programming box 160A displays the total stimulation current amplitude for the lead 140 as 0.35 mA and the pulse width as 200 µs. Pulse width is defined as the time duration of a single stimulation pulse.

The programming box 160B displays the percentage of current being distributed to the electrode 150B as 100%. The value of this percentage is between 0 and 100. In more detail, for a neurostimulator, the amount of current sourced by a first set of electrodes should be equal to the amount of current sunk by a second set of electrodes. Each electrode in the first set should be assigned to source a certain percentage of the sourced current, and the sum of the percentages should be equal to 100%. Similarly, each electrode in the second set should be assigned to sink a certain percentage of the sunk current, and the sum of the percentages should also be equal to 100%. In the example shown in FIG. 2, the anode electrode 150B is assigned to handle 100% of the current.

The programming box 160C displays the current amplitude range, which has a lower limit and an upper limit. The lower limit corresponds to a perceived stimulation threshold, which is the minimum stimulation pulse strength that a patient is able to perceive. The upper limit corresponds to a pain threshold, which is the stimulation pulse strength that begins to cause pain to the patient. The user (e.g., physician) may be allowed to set a target current amplitude range to a value between the perceived stimulation threshold and the pain threshold.

The programming box 160D is used to assign a contact polarity to the selected contact.

It is understood that additional programming boxes may be utilized to display other stimulation programming parameters, but they are not illustrated or discussed herein for the sake of simplicity.

The program window 105A further includes a virtual control mechanism 170 that can be used to adjust the values of the stimulation parameters in the programming boxes 160. In the embodiment shown herein, the virtual control mechanism includes "+" and "−" buttons that are used to increment and decrement the values of the stimulation parameters, respectively. In other embodiments, additional suitable virtual control mechanisms such as toggles, switches, or text/numerical input fields may be used instead. It is understood that the virtual control mechanism 170 may also be viewed as a programming box in certain embodiments.

The program window 105A further includes a plurality of icons 180-188 that facilitate the programming of stimulation parameters. The icon 180 is a "back" icon and enables the user to navigate to a previous screen. The icon 181 is a "patient menu" icon and enables patient-related menu items to be shown. The icon 182 is a "clinician menu" icon and enables clinician-related menu items to be shown. The icon 183 is a "lead toggle" icon and toggles the selection of the leads (when there are multiple leads). The icon 184 is a "CASP" icon. CASP stands for Computer Assisted Stimulation Programming. The intent is to provide electrodes (contacts) that address the pain areas for stimulation. The icon 185 is an "impedance check" icon and allows an impedance check to be performed to evaluate whether an electrical short or electrical open condition exists. The icon 186 is a "mode toggle" icon and toggles between different input modes for the current amplitude assignment for the electrodes. For example, the current amplitude assignment shown in FIG. 2 is done in a percentage mode (as indicated by the 100% assigned to the anode 150B in the programming box 160B).

Still referring to FIG. 2, the icon 187 is a "stimulation map" icon and allows the association and display of a customized and patient-defined stimulation map with the stimulation program. In some embodiments, the icon 187 or another similar icon may be used to display a customized and patient-defined "pain map" as well. The various aspects of the stimulation map and pain map will be discussed in greater detail later. Still referring to FIG. 2, the icon 188 is a "settings" icon and allows different settings involving the user interface 100 to be configured.

It is understood that the user interface herein may show lead orientation in addition to showing the contacts parameters. The display of lead orientation helps guide the healthcare professional where the contact is relative to the spinal cord. Furthermore, the user interface herein allows for the capability to program multiple leads at once if the leads are in close proximity to each other. The same scenario with the leads farther apart (for example lead 1 on C1 and lead 2 on T1, refer to FIG. 16A for C1 and T1) would program the leads separately. FIG. 2 shows both leads' contact because they occupy the same space.

Figure 3:
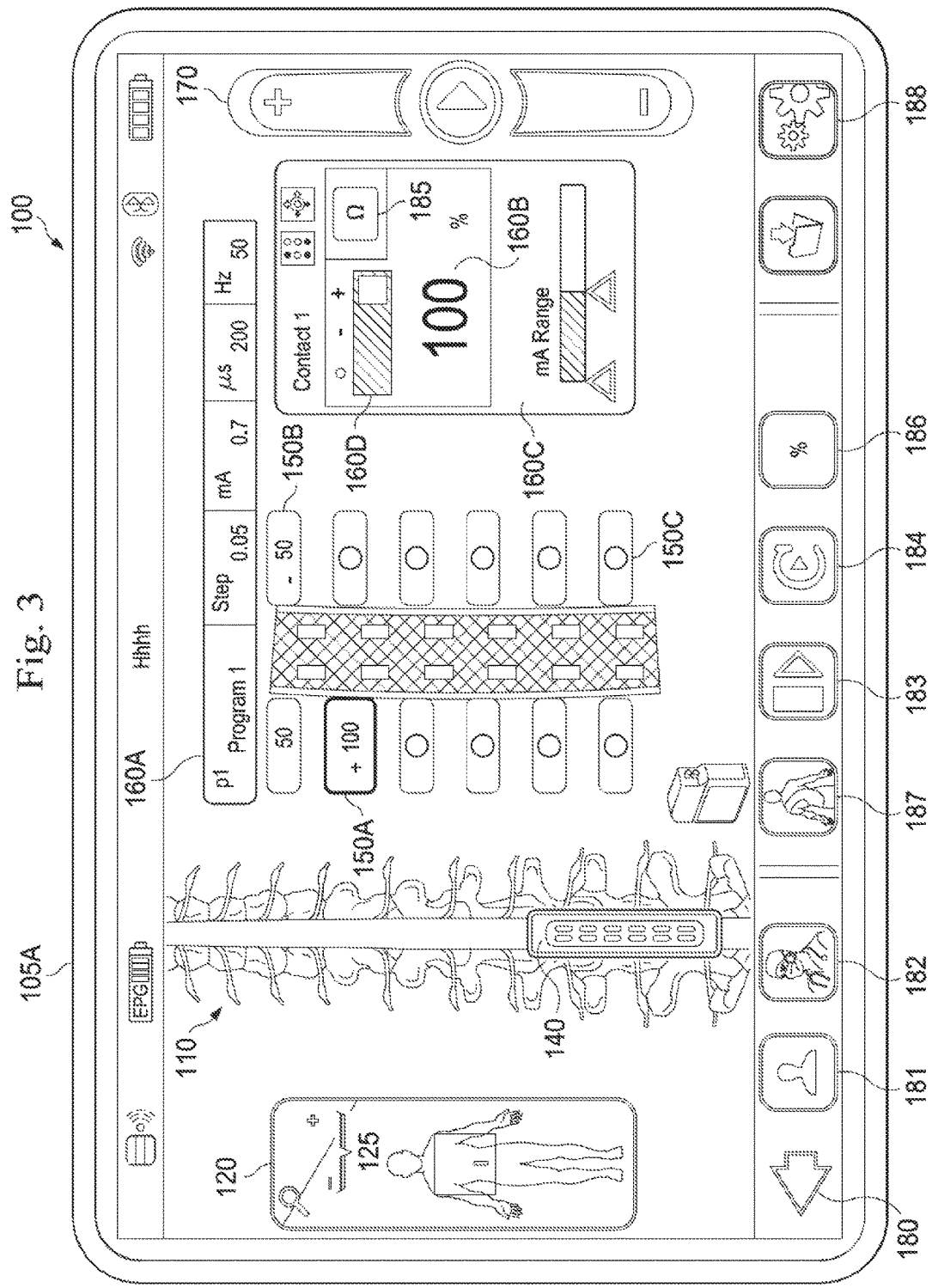

Referring now to FIG. 3, the program window 105A shows another example programming screen for a single 12 contact lead. Of these contacts, an anode 150A and two cathodes 150B are being programmed. The anode 150A is assigned 100% of the current, and the two cathodes 150B are each assigned 50% of the current, where the total current is 0.7 mA. Note that the user can toggle between different leads when multiple leads are used, such as in FIG. 2. But since only one lead is used in FIG. 3, no lead toggling is necessary. The current assignment is done in a percentage mode as shown in FIGS. 2-3, but it is also envisioned that a numerical entry mode may also be used to assign currents in alternative embodiments. The numerical entry mode is not illustrated herein for reasons of simplicity.

The program windows 105A shown in FIGS. 2-3 illustrate how a group of stimulation parameters can be displayed and configured. As discussed above, the group of stimulation parameters (or their configuration) corresponds to a "stimulation program." The stimulation program resides within a lower level of the hierarchy of the user interface 100. When there are multiple stimulation programs, they may collectively form a "stimulation program-set." The stimulation program-set resides in a middle level of the hierarchy of the user interface 100. In other words, the stimulation program-set sits one level above the stimulation program.

Figure 4:
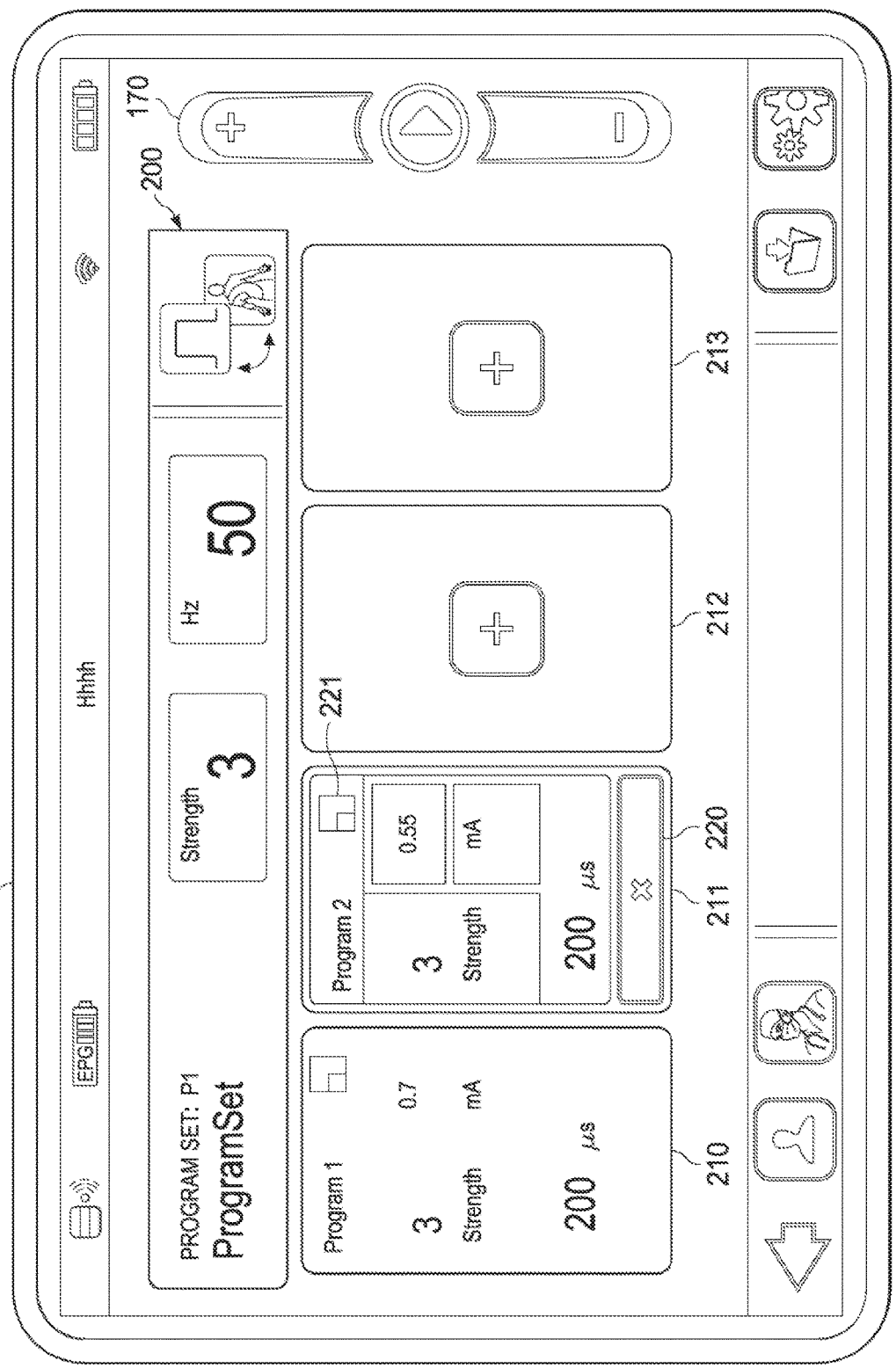

FIG. 4 shows a program window 105B (or programming screen) that displays a visual representation of a stimulation program-set 200 according to one embodiment. The example stimulation program-set 200 includes the visual representations of a plurality of stimulation programs, four of which are shown in programming boxes 210-213 herein as examples. Specifically, the stimulation programs (i.e., Program 1 and Program 2) in the programming boxes 210-211 are programs whose stimulation parameters have already been configured. The stimulation programs in the programming boxes 212-213 are empty programs whose stimulation parameters have yet to be configured and are thus empty programs. For Program 1 and Program 2, their respective visual representations contain stimulation parameter information such as the current amplitude and pulse width associated with each stimulation program. In this manner, each stimulation program is visually abstracted as a programming box as a part of the stimulation program-set 200 (i.e., the middle level of the hierarchical user interface).

The programming boxes 210-213 can be selected individually to perform additional management tasks. For example, as shown in FIG. 4, the programming box 211 is selected, so that further management tasks can be performed to the stimulation program 2. A plurality of icons 220-221 may be used to perform these management tasks. In an embodiment, the icon 220 allows the stimulation program 2 to be removed from the stimulation program-set 200. The icon 221 allows the stimulation program 2 to be edited and navigates to the programming screen in FIG. 2 or 3.

The stimulation parameters of each stimulation program can be edited through the virtual control mechanism 170, which is substantially the same as the one discussed above with reference to FIG. 2. These stimulation parameters specific to each individual stimulation program may be referred to as "local" stimulation parameters. In addition, "global" stimulation parameters—the stimulation parameters for the entire stimulation program-set—can also be edited. For example, referring to FIG. 5, the program window 105B may include a programming box 214 that can be used to display the global stimulation parameters of the entire stimulation program-set 200. In the embodiment shown, the global stimulation parameter is the stimulation frequency (shown as 50 Hz), although other global stimulation parameters may be used in alternative embodiments. Once again, the global stimulation parameter shown in the programming box 214 can also be set by the virtual control mechanism 170.

The stimulation programs populating the stimulation program-set 200 can be executed one at a time, for instance in a sequential manner. As an example, the stimulation program 1 (represented by the programming box 210) can be executed first, followed by the stimulation program 2 (represented by the programming box 211), so on and so forth. After all the stimulation programs are executed, the process can be repeated any number of times.

The execution of each stimulation program may last a relatively short period, for example a number of milliseconds. As a result, the patient may not be able to distinctly experience the execution of each stimulation program. If the stimulation program 1 is targeted toward a first area of the patient's body (e.g., upper neck), and the stimulation program 2 is targeted toward a second area of the patient's body (e.g., lower neck), then the execution of stimulation programs 1 and 2 may allow the patient to "feel" like both the first area and the second area of his body are being treated. In this manner, the stimulation program-set offers a more comprehensive and more effective treatment to the patient, since it allows targeted stimulation of multiple areas of the patient's body almost simultaneously.

Figure 5:
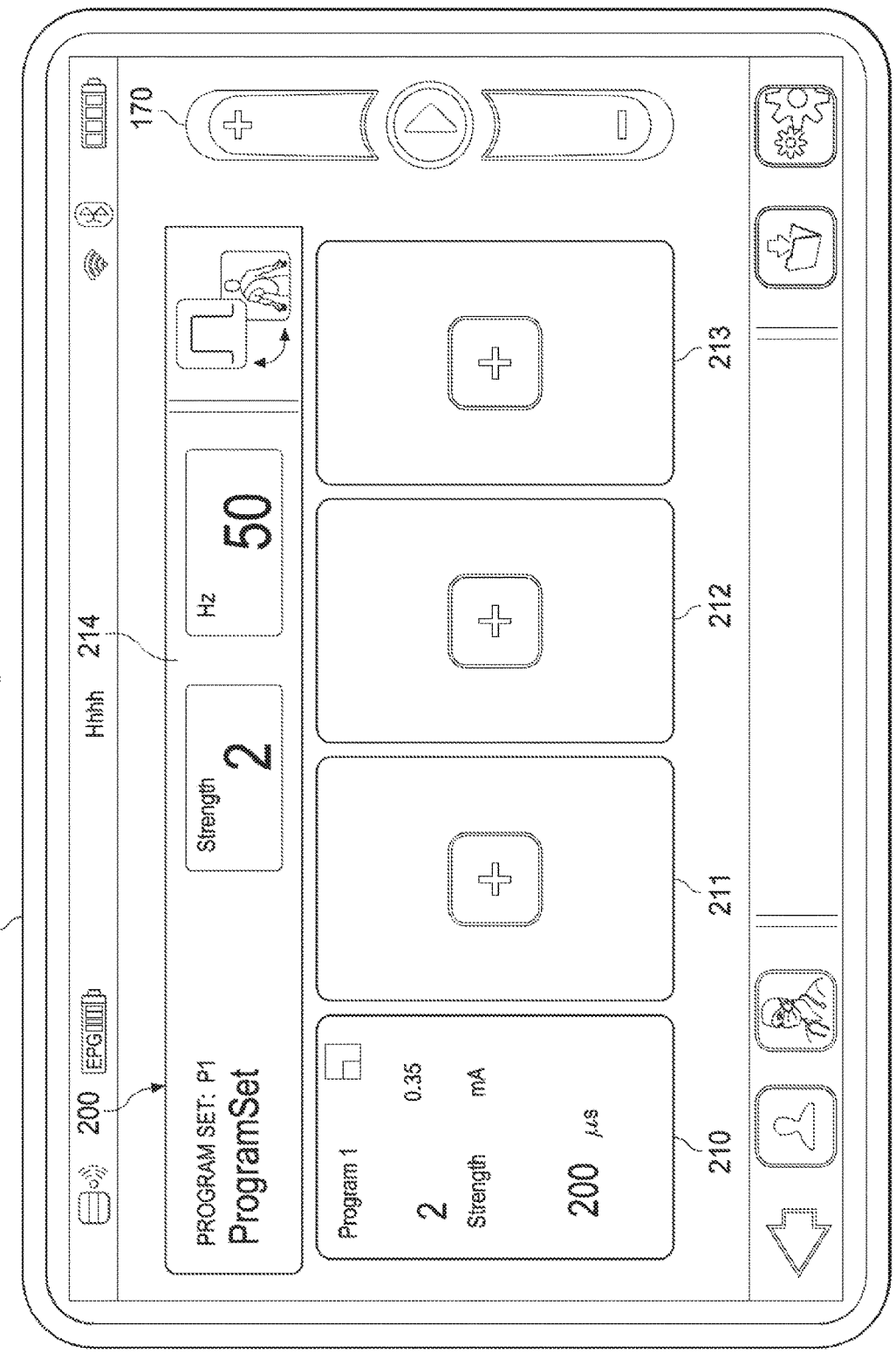
Figure 6:
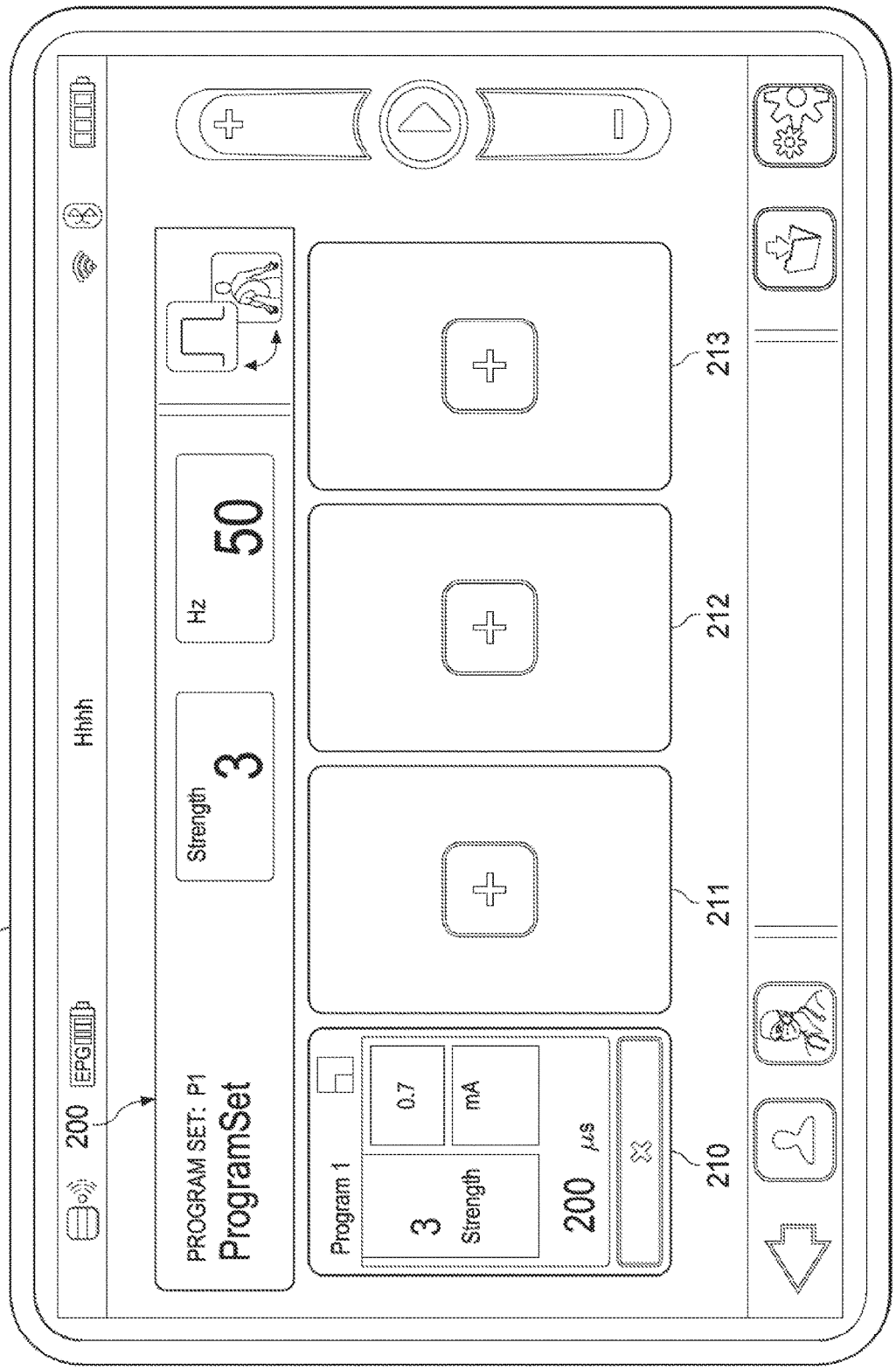

The program windows 105B shown in FIGS. 4-6 illustrate how a collection of stimulation programs can be displayed and configured in the form of a "stimulation program-set." The stimulation program-set resides within a middle level of the hierarchy of the user interface 100, which is at least one level above the lower level where the stimulation programs reside. When there are multiple stimulation program-sets, they may be collectively represented by a "stimulation program-set list." The stimulation program-set list resides in an upper level of the hierarchy of the user interface 100. In other words, the stimulation program-set list sits one level above the stimulation program-set.

Figure 7:
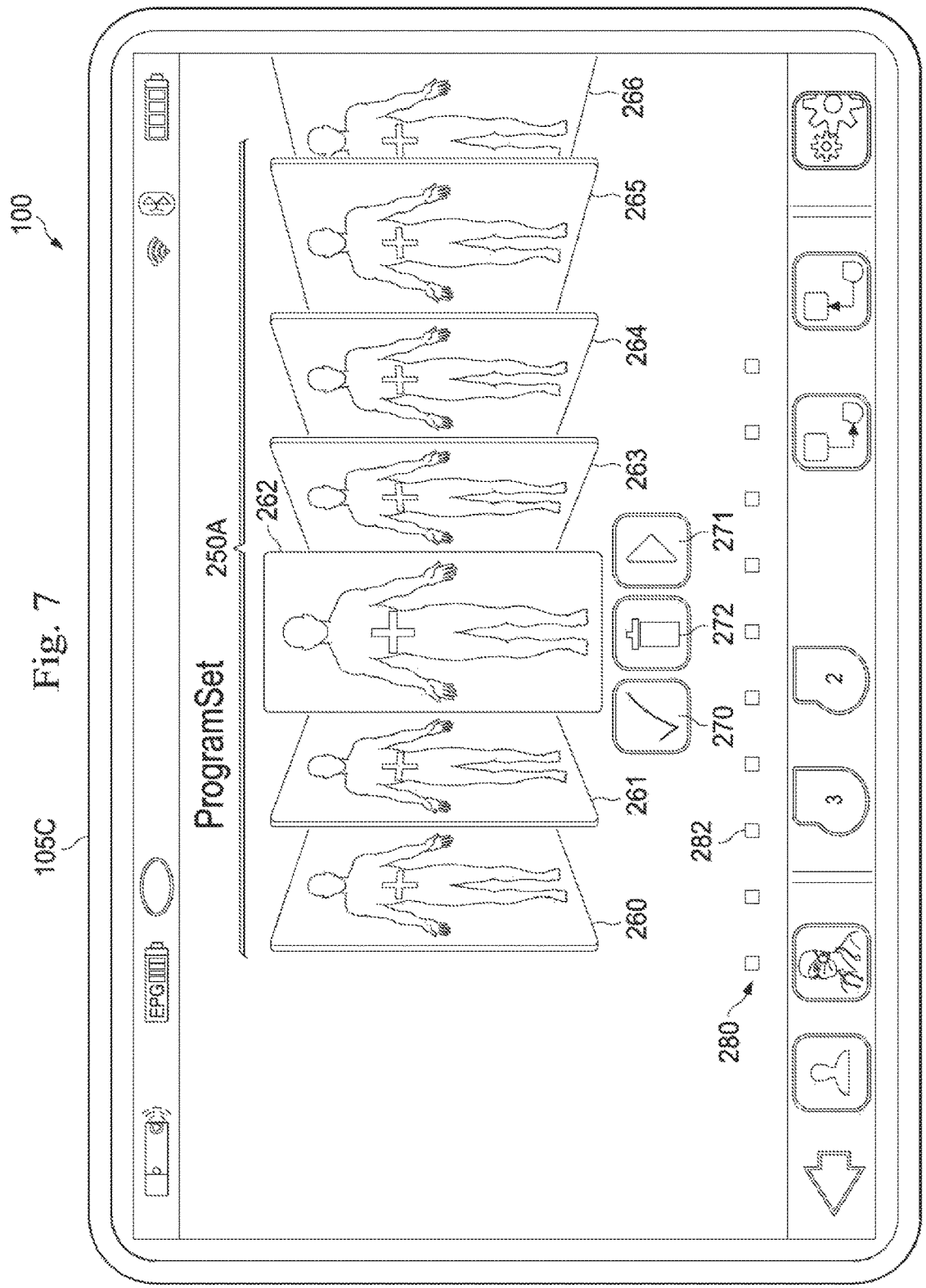

FIG. 7 shows a program window 105C that displays a visual representation of a stimulation program-set list 250A according to one embodiment. The example stimulation program-set list 250A includes the visual representations of a plurality of stimulation program-sets, for example stimulation program-sets 260-266 shown herein. The stimulation program-sets 260-266 may each contain a collection of configured stimulation programs or may be empty (i.e., not containing any stimulation programs but is ready to have stimulation programs added thereto). In the embodiment shown, the "+" mark displayed on each stimulation program-set indicates that it is an empty stimulation program-set.

The stimulation program-sets 260-266 are each visually represented herein as a three-dimensional (3-D) virtual card. Alternatively stated, each stimulation program-set is visually abstracted as a respective 3-D virtual card. These virtual cards are collectively organized into a scrollable virtual carousel. As a user spins the carousel, for example by moving his finger to the left or right on a touch screen on which the program window 105C is displayed, different virtual cards corresponding to their respective stimulation program-sets 260-266 may be brought to the front of the carousel.

The stimulation program-set at the front of the carousel (the stimulation program-set 262 in this case) may be considered an active selection of the user, i.e., the stimulation program-set is ready for management or execution. For example, if the selected stimulation program-set 262 has one or more stimulation programs stored therein, it can be activated through a click of an "activation" icon 270, and thereafter executed through a click of an "execution" icon 271. Furthermore, the selected stimulation program-set 262 can be deleted from the virtual carousel through a click of a "delete" icon.

To facilitate the user's understanding of the user interface 100, a row of indicators 280 is displayed in the program window 105C. The row of indicators 280 contains a plurality of indicators that each correspond to a respective one of the stimulation program-sets. When a stimulation program-set is selected, the corresponding indicator is highlighted as well.

For example, as the stimulation program-set 262 is selected, the indicator 282 is highlighted, while the rest of the indicators remain dark. As the user navigates through the virtual carousel (by spinning the carousel), different stimulation program-sets are selected, and correspondingly different indicators of the row of indicators 280 will become highlighted to track the selected stimulation program-set.

Figure 8:
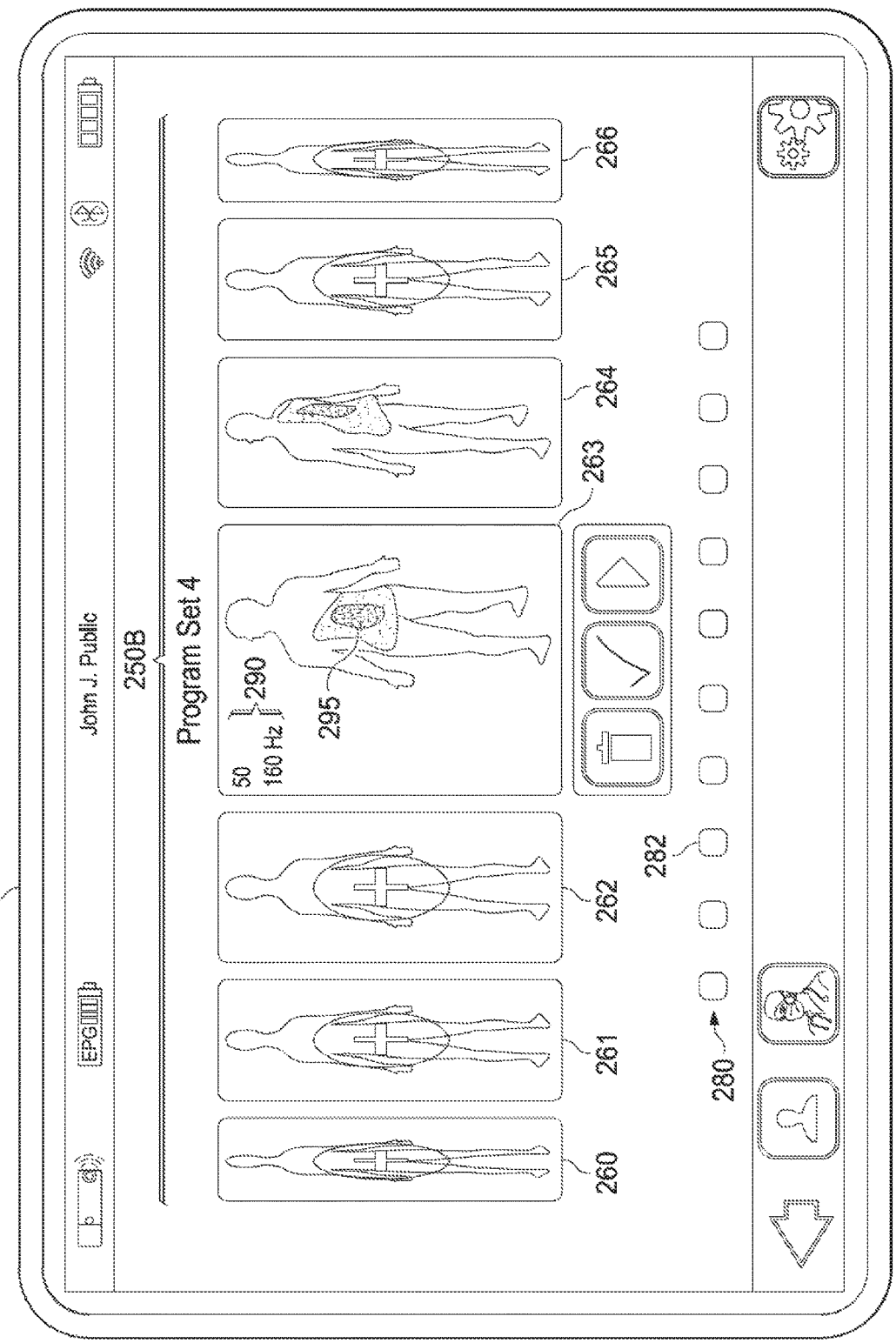

FIG. 8 shows a program window 105C that displays a visual representation of the stimulation program-set list 250B according to another embodiment. Similar to the stimulation program-set list 250B discussed above and illustrated in FIG. 7, the stimulation program-set list 250B of FIG. 8 also includes the visual representations of a plurality of stimulation program-sets 260-266 as examples. Some of these stimulation program-sets may each contain a collection of configured stimulation programs, such as the stimulation program-sets 263-264, while other stimulation program-sets may be empty, for example the stimulation program-sets 260-262 and 265-266.

In the embodiment shown, the "+" marks displayed on the stimulation program-sets 260-262 and 265-266 indicate that they are empty stimulation program-sets. On the other hand, the non-empty stimulation program-sets 263-264 each display one or more stimulation parameters 290 and a stimulation map 295. The stimulation parameters 290 may include "global" stimulation parameters that apply to all the stimulation programs within the particular stimulation program-set. For example, current amplitude percentile level (e.g., 50% in FIG. 8) and stimulation frequency (e.g., 160 Hz in FIG. 8) may be considered global stimulation parameters in the illustrated embodiment.

The stimulation map 295 is a customizable patient-defined stimulation map. In more detail, the patient may be allowed to draw or paint a stimulation map 295 with arbitrary boundaries in response to the stimulation he experiences. The patient's input is recorded via the touch-sensitive screen, which is configured to detect the movement of the patient's finger(s) or a stylus or another suitable input mechanism on the screen. The boundaries of the stimulation map 295 are arbitrary in the sense that they are delineated by the movements of the user's finger(s) on the touch-sensitive screen. Thus, the patient-defined stimulation map can track the patient's stimulation experience with precision. In comparison, many existing methods of generating and displaying stimulation maps rely on the patient to select one or more predefined boxes or regions to represent the stimulation he experiences, which is crude and imprecise.

The stimulation map 295 discussed herein may also allow the patient to indicate the intensity of stimulation through different color codes. Each color-shaded region may correspond to a different level of stimulation intensity experienced by the patient. In certain embodiments, the stimulation map 295 is drawn on a rotatable and scalable three-dimensional human body model. The patient-defined stimulation map may be generated and stored either locally on the electronic programmer or in a remote server in a "cloud." In some other embodiments, a customizable patient-defined pain map may be generated in response to the patient's input in a manner similar to the generation of the stimulation map 295. The pain map reflects the pain experienced by the patient. The program window 105C may display such pain map in addition to, or instead of, the stimulation map 295.

Figure 9:
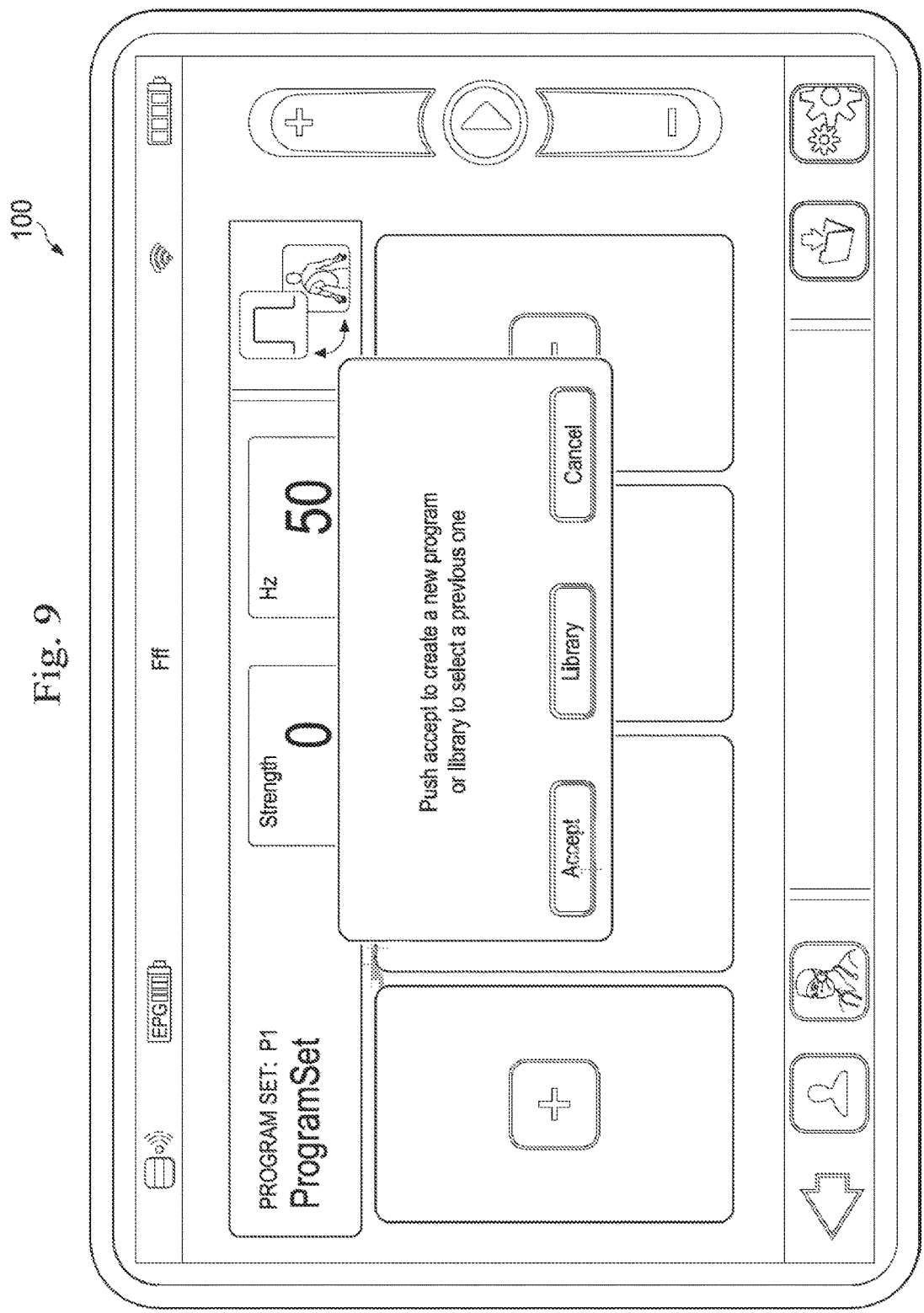
Figure 10:
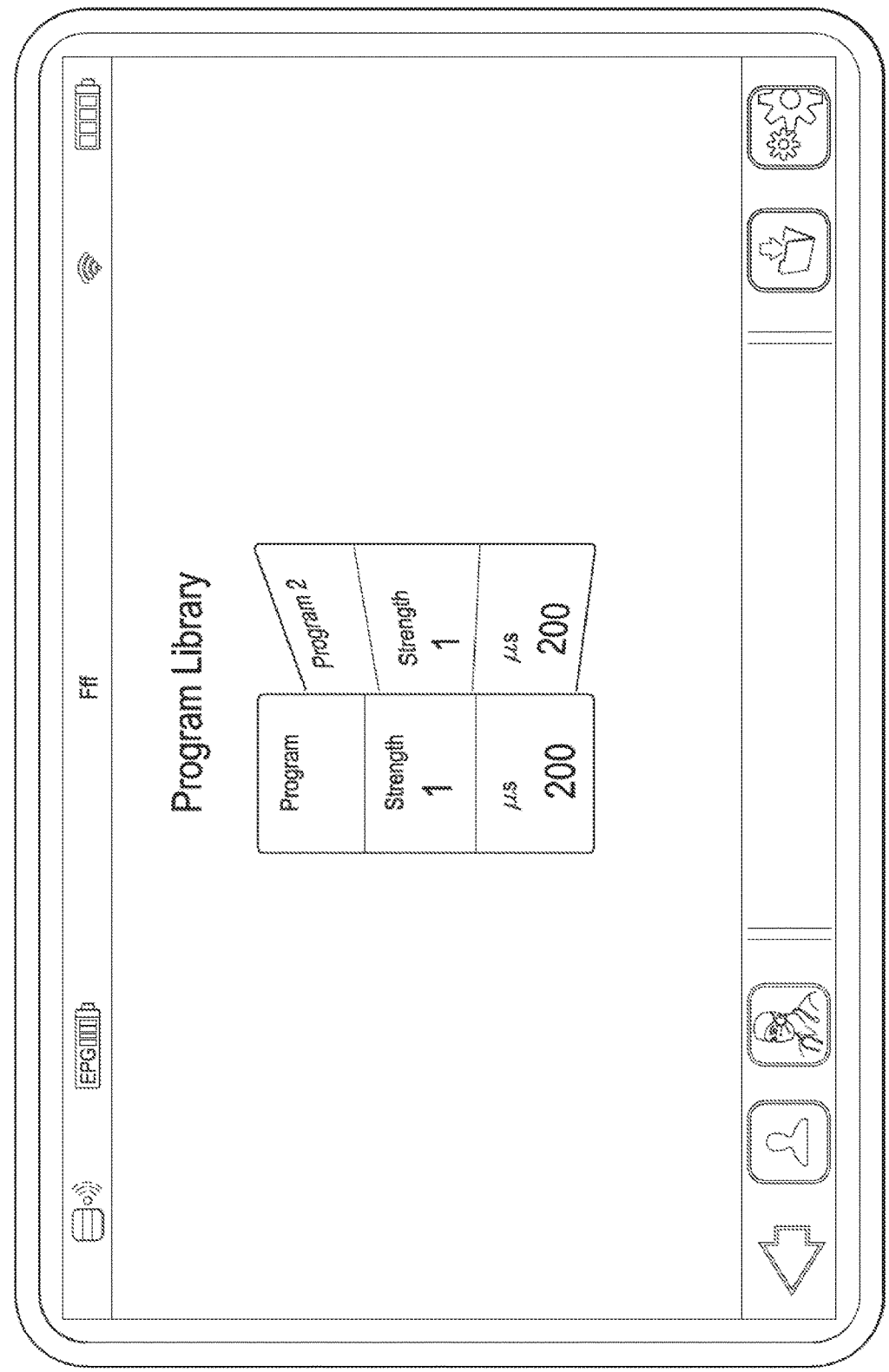

It is understood that the user interface 100 discussed herein allows a user to copy the contents of an existing program to a new program. Within a program-set, if the user decides to create a new program, the user is given a choice to either start a new program from scratch or use an existing program as a starting point. FIGS. 9-10 illustrate example screenshots of the user interface 100 for allowing the user to copy the contents of an existing program to a new program.

The program windows 105C shown in FIGS. 7-10 illustrate how a collection of stimulation program-sets can be displayed and configured as a scrollable list, for example in the form of a spinnable virtual carousel. The stimulation program-set list (such as the list 250A-250B) resides within an upper level of the hierarchy of the user interface 100, which is at least one level above the middle level where the stimulation program-sets reside, and at least two levels above the lower level where the stimulation programs reside. As such, the user interface 100 of the present disclosure provides a visual representation of a medical therapy by utilizing a plurality of abstracted hierarchy levels to display the various stimulation parameters, programs, program-sets, and program-set list. Such abstracted hierarchical approach allows the user to view and manage a large number of stimulation parameters (or groups of stimulation parameters) quickly and efficiently.

It is understood that in addition to configuring the stimulation programs through manual programming, the stimulation programs may also be automatically synchronized with a medical device such as a pulse generator. For example, the stimulation programs may be "pulled" from the pulse generator, which may already contain active stimulation programs. Vice versa, the stimulation programs may also be "pushed" to the pulse generator from an electronic programmer. Furthermore, multiple stimulation programs may be merged together, and some of the stimulation programs may also be overridden.

Figure 11:
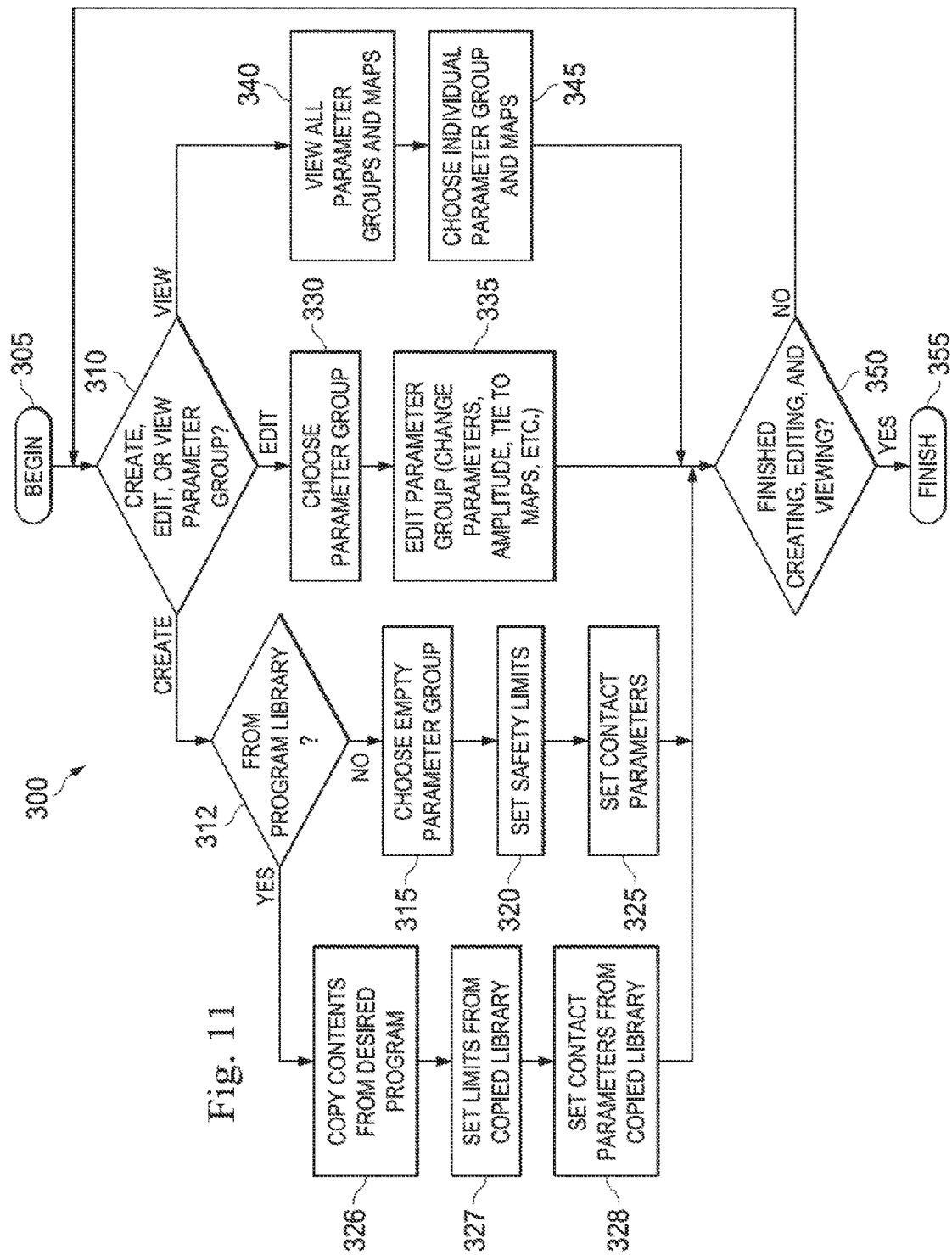
FIGS. 11-13 are flowcharts of methods for configuring parameters of a medical therapy according to various aspects of the present disclosure.

FIG. 11 illustrates a method 300 of configuring one or more stimulation programs according to some embodiments of the present disclosure. In certain embodiments, the various steps of the method 300 may be performed by one or more electronic processors in response to user input. In some other embodiments, the various steps of the method 300 may be performed by the user, which may be a healthcare professional, for example a clinician or a surgeon. For the discussions that follow, it is understood that a stimulation program may also be referred to as a parameter group, or vice versa.

The method 300 begins at step 305, which may involve selecting an appropriate medical device for which a stimulation program is to be configured. The method 300 continues to a decision step 310 to determine whether a parameter group (i.e., a stimulation program) should be created, edited, or viewed. If the answer from the decision step 310 is that a parameter group should be created, the method 300 proceeds to a decision step 312 to see whether the creation comes from a program library. If the answer is no, then the method 300 proceeds to step 315 to choose an empty parameter group. After an empty parameter group is chosen, the method 300 proceeds to step 320 to set safety limits for the parameter group. The setting of the safety limits is described in more detail in U.S. patent application Ser. No. 13/601,504, filed on Aug. 31, 2012, entitled "TOUCH SCREEN SAFETY CONTROLS FOR CLINICIAN PROGRAMMER", the content of which are herein incorporated by reference in its entirety. After the safety limits are set, the method 300 proceeds to step 325 to set the contact (i.e., electrodes) parameters, which may include electrode polarity, frequency, pulse width, current amplitude, voltage amplitude, and whether a lead is active or inactive. On the other hand, if the answer from the decision step 312 is yes, then the method 300 proceeds to step 326 to copy contents from the desired program. Then the method 300 proceeds to step 327 to set limits from the copied library. The method 300 also proceeds to step 328 to set contact parameters from the copied library.

If the answer from the decision step 310 is that a parameter group should be edited (i.e., a parameter group already exists and needs to be modified), the method 300 proceeds to step 330 to choose the parameter group. After the desired parameter group is chosen, the method 300 proceeds to step 335 to edit the parameters of the parameter group. For example, step 335 may involve selecting additional electrodes for programming, changing the stimulation amplitude of electrodes, associating the parameters to maps such as stimulation maps and/or pain maps, etc.

If the answer from the decision step 310 is that existing parameter groups and their associated maps should be viewed, the method 300 proceeds to step 340 to begin the viewing of all parameter groups and their associated maps (stimulation maps and/or pain maps). Individual parameter groups and maps may also be viewed in step 345.

After the execution of steps 325, 335, and 345, the method 300 proceeds to another decision step 350 to determine whether the creating, editing, and viewing of parameter groups has been completed. If the answer is no, then the method 300 loops back to the decision step 310 again to repeat the execution of the steps discussed above. If the answer is yes, the method 300 will finish at step 355.

Figure 12:
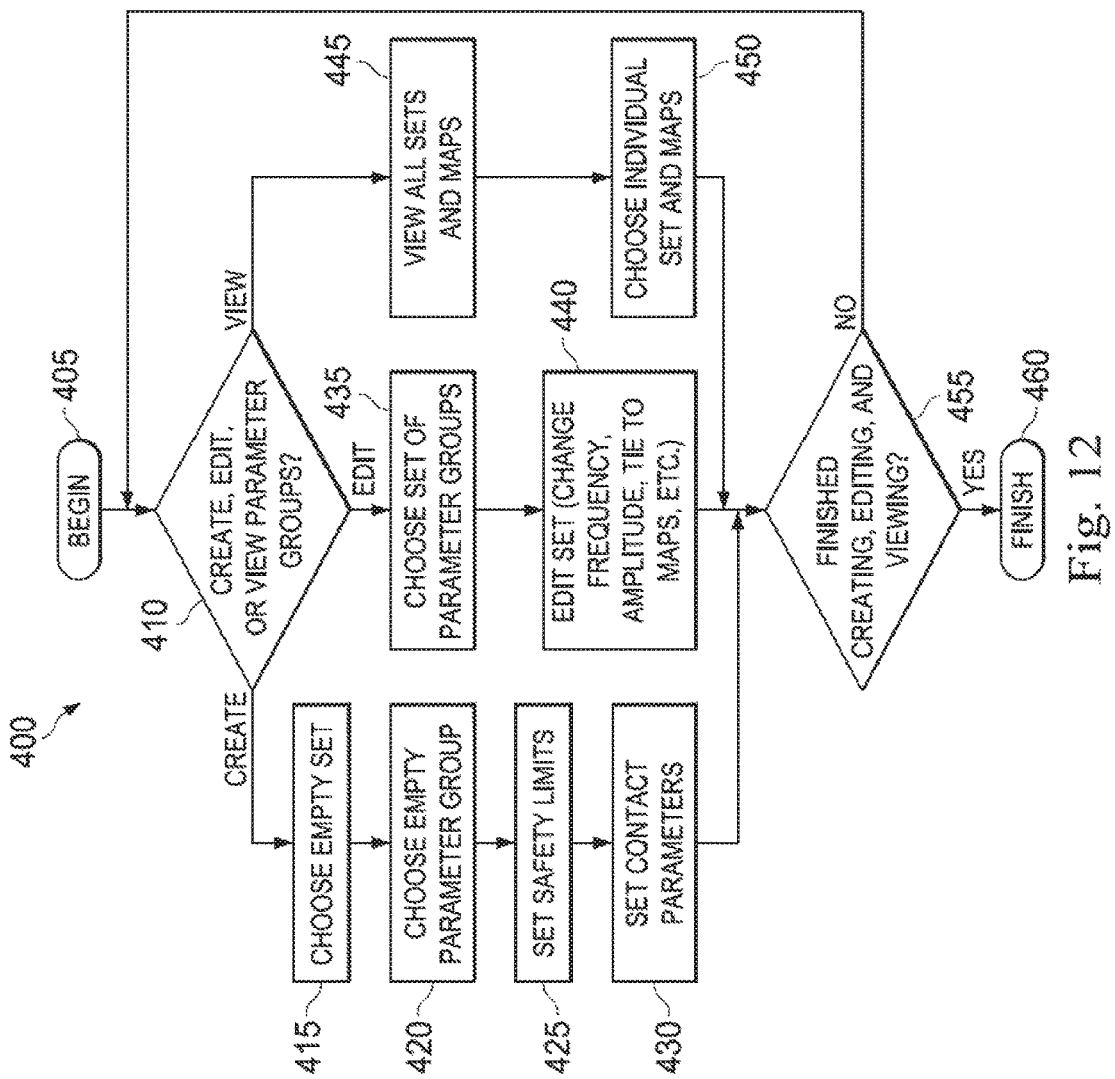

FIG. 12 illustrates a method 400 of configuring one or more stimulation program-sets according to some embodiments of the present disclosure. In certain embodiments, the various steps of the method 400 may be performed by one or more electronic processors in response to user input. In some other embodiments, the various steps of the method 400 may be performed by the user, which may be a healthcare professional, for example a clinician or a surgeon. For the discussions that follow, it is understood that a stimulation program-set may also be referred to as a set of parameter groups, or vice versa.

The method 400 begins at step 405, which may involve selecting an appropriate medical device for which a stimulation program is to be configured. The method 400 continues to a decision step 410 to determine whether a set of parameter groups (i.e., a stimulation program-set) should be created, edited, or viewed. If the answer from the decision step 410 is that a parameter group should be created, the method 400 proceeds to step 415 to choose an empty set of parameter groups. Thereafter, the method 400 proceeds to step 420 to choose an empty parameter group. After an empty parameter group is chosen, the method 400 proceeds to step 425 to set safety limits for the parameter group. After the safety limits are set, the method 400 proceeds to step 430 to set the contact (i.e., electrodes) parameters, which may include electrode polarity, frequency, pulse width, current amplitude, voltage amplitude, and whether a lead is active or inactive.

If the answer from the decision step 410 is that a set of parameter groups should be edited (i.e., a set of parameter groups already exists and needs to be modified), the method 400 proceeds to step 435 to choose the set of parameter groups for editing. After the desired set of parameter groups is chosen, the method 400 proceeds to step 440 to edit the set. For example, step 440 may involve changing the stimulation frequency, stimulation amplitude, and association of maps such as stimulation maps and/or pain maps with the set of parameter groups, etc.

If the answer from the decision step 410 is that existing sets of parameter groups and their associated maps should be viewed, the method 400 proceeds to step 445 to begin the viewing of all sets of parameter groups and their associated maps (stimulation maps and/or pain maps). Individual sets of parameter groups and maps may also be viewed in step 450.

After the execution of steps 430, 440, and 450, the method 400 proceeds to another decision step 455 to determine whether the creating, editing, and viewing of the sets of parameter groups has been completed. If the answer is no, then the method 400 loops back to the decision step 410 again to repeat the execution of the steps discussed above. If the answer is yes, the method 400 will finish at step 460.

Figure 13:
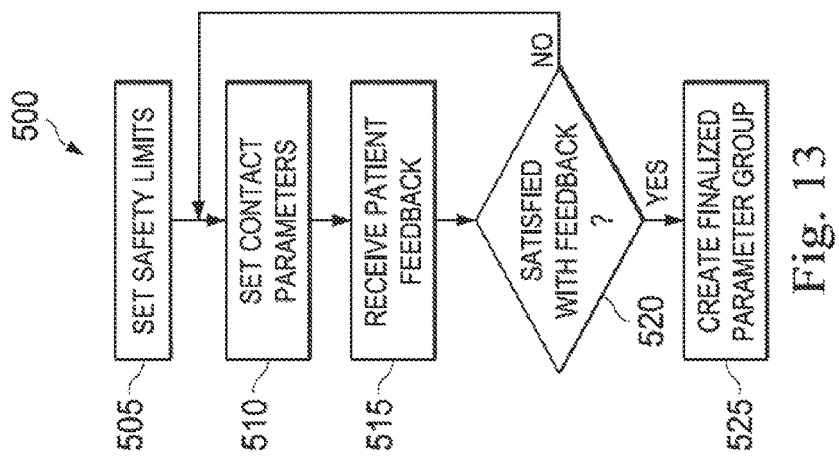

FIG. 13 illustrates a method 500 of configuring the stimulation parameters from a healthcare provider's perspective according to some embodiments of the present disclosure. The method 500 beings with step 505 to set the safety limits of the stimulation parameter programming. Again, the setting of the safety limits is described in more detail in U.S. patent application Ser. No. 13/601,504, filed on Aug. 31, 2012, entitled "TOUCH SCREEN SAFETY CONTROLS FOR CLINICIAN PROGRAMMER", the content of which are herein incorporated by reference in its entirety.

The method 500 continues with step 510 to set the contact parameters (i.e., programming the parameters for the various electrodes). The parameters may include electrode polarity, frequency, pulse width, current amplitude, voltage amplitude, and whether a lead is active or inactive.

The method 500 continues with step 515, in which patient feedback is received. The patient feedback may include a description of the stimulation or pain sensations experienced by the patient in response to the stimulation therapy. The patient may also be asked to generate a stimulation map or a pain map based on his experience.

The method 500 continues with step 520 to determine whether the healthcare provider is satisfied with the feedback received from the patient. If the answer is no, then the method 500 loops back to step 510 again to adjust the programming of the contact parameters. On the other hand, if the answer is yes, then the method 500 proceeds to step 525 to create a finalized parameter group.

Figure 14:
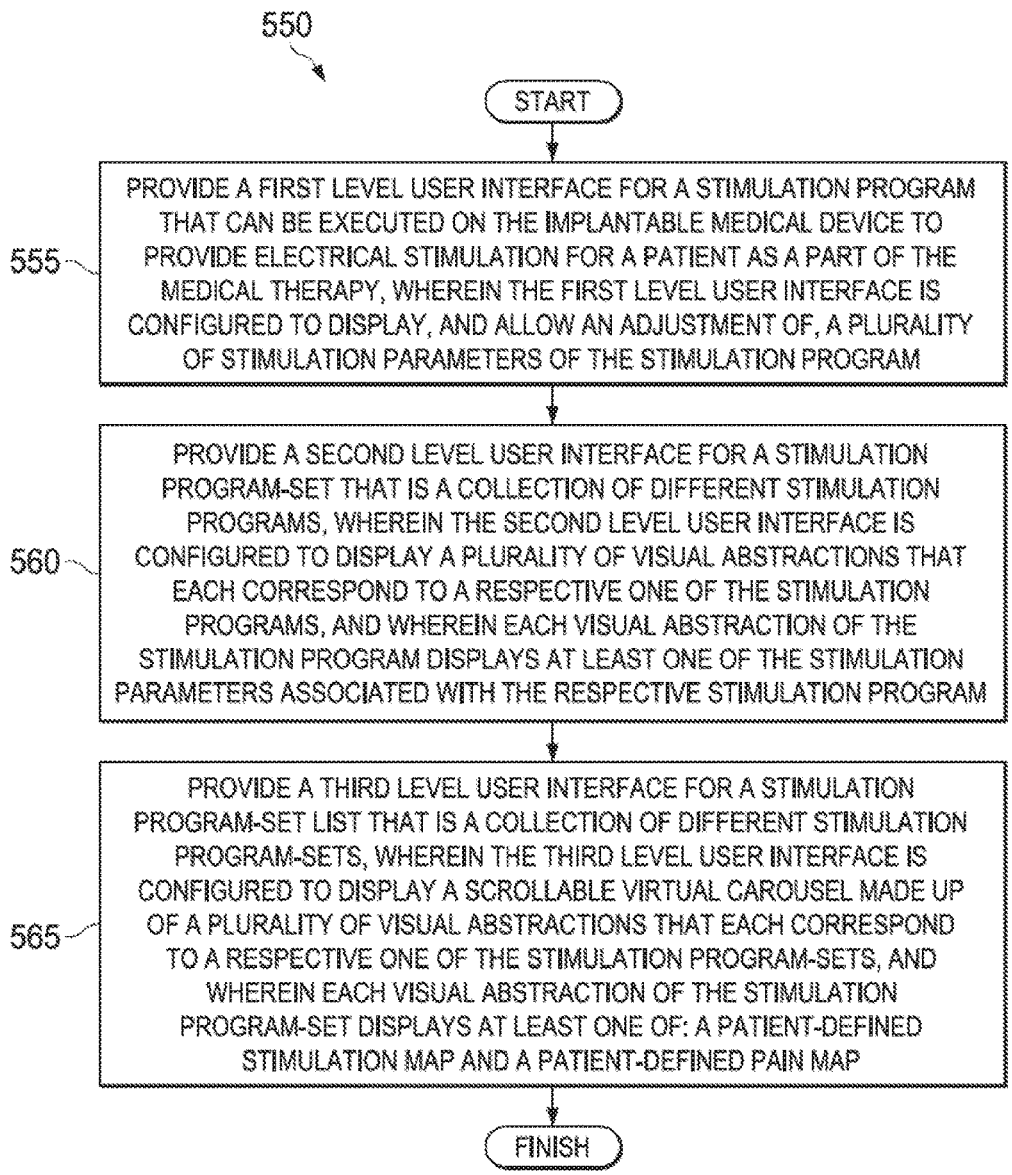
FIG. 14 is a flowchart for a method of visualizing medical therapy according to various aspects of the present disclosure.

FIG. 14 is a flowchart for a method 550 of visualizing medical therapy associated with an implantable medical device. The method 500 includes a step 555, in which a first level user interface for a stimulation program is provided. The stimulation program can be executed on the implantable medical device to provide electrical stimulation for a patient as a part of the medical therapy. The first level user interface is configured to display, and allow an adjustment of, a plurality of stimulation parameters of the stimulation program. In some embodiments, the first level user interface is further configured to display a virtual representation of the implantable medical device and its target anatomical environment. In some embodiments, the access of the first level user interface by the patient is denied. In other words, the access of the user interface is restricted to a healthcare professional.

The method 500 includes a step 560, in which a second level user interface for a stimulation program-set is provided. The stimulation program-set is a collection of different stimulation programs. The second level user interface is configured to display a plurality of visual abstractions that each correspond to a respective one of the stimulation programs. Each visual abstraction of the stimulation program displays at least one of the stimulation parameters associated with the respective stimulation program. In some embodiments, the second level user interface is further configured to display a stimulation parameter that is common to all of the stimulation programs within the stimulation program-set.

The method 500 includes a step 565, in which a third level user interface for a stimulation program-set list is provided. The stimulation program-set is a collection of different stimulation program-sets. The third level user interface is configured to display a scrollable virtual carousel. The virtual carousel is made up of a plurality of visual abstractions that each correspond to a respective one of the stimulation program-sets. Each visual abstraction of the stimulation program-set displays at least one of: a patient-defined stimulation map and a patient-defined pain map. In some embodiments, the third level user interface is further configured to display, on each visual abstraction of the stimulation program-set, a stimulation parameter that is common to all of the stimulation programs within the stimulation program-set.

In some embodiments, the first level user interface, the second level user interface, and the third level user interface is displayed one at a time on a touchscreen device. In some embodiments, the first level user interface, the second level user interface, and the third level user interface are each implemented on a portable electronic device that is one of: a clinician programmer, a patient programmer, and a computer tablet.

It is understood that the steps 555-565 described herein are merely example steps according to some embodiments. These steps may be omitted or modified in certain embodiments. In certain other embodiments, the method 500 may also include additional steps performed before, during, or after the steps 555-565. As an example, the method 500 may include a step to generate the patient-defined stimulation map or the patient-defined pain map in response to patient input. The boundaries of the stimulation map and the pain map may be customizable and defined by the patient. As another example, the method 500 may include a step to select a target stimulation program-set for execution and then executing each of the stimulation programs in the stimulation program-set.

The hierarchical visual representation of a medical therapy according to the various aspects of the present disclosure offers advantages over existing methods of representing medical devices. It is understood, however, that not all advantages are discussed herein, different embodiments may offer different advantages, and no embodiment is limited to particular advantages.

One advantage of the present disclosure is that a virtual reality environment is available for programming and viewing stimulation parameters or stimulation programs containing these parameters. The user is able to navigate through or view representations of multiple groups of parameters at the same time. For example, multiple groups of parameters may be represented by a plurality of corresponding digital cards containing relevant stimulation-related information in a carousel-like view.

Another advantage of the present disclosure is that pain maps or stimulation maps can be associated with groups of parameters. The pain maps or stimulations are customizable according to patient input and therefore are more precise and more accurately reflect the patient's experience. The association of the pain/stimulation maps with their corresponding stimulation program allows the clinician to quickly select a suitable treatment program to target one or more particular pain areas. For example, a clinician may quickly navigate through multiple sets of stimulation programs or stimulation program-sets to see which ones are targeting neck pain and select one or more suitable programs accordingly. Moreover, as the treatment of the patient continues, the pain/stimulation maps or the parameters of their associated stimulation programs may be continuously updated to track the patient's experience. The clinician may also view previously-stored stimulation programs and their associated pain/stimulation maps to see whether there is a migratory pattern with respect to the pain or stimulation.

Another advantage of the present disclosure is that the parameter groups are easily manageable, for example the naming, renaming, deleting, and locking (preventing further modifications) of the parameter groups. Creation of local or remote libraries of parameter groups and associated pain or stimulation maps is also enabled.

It is understood that the various aspects of the present disclosure are applicable to any type of neural stimulation. The discussions above use spinal cord stimulation only as an example, but it is not intended to be limiting.

Figure 15:
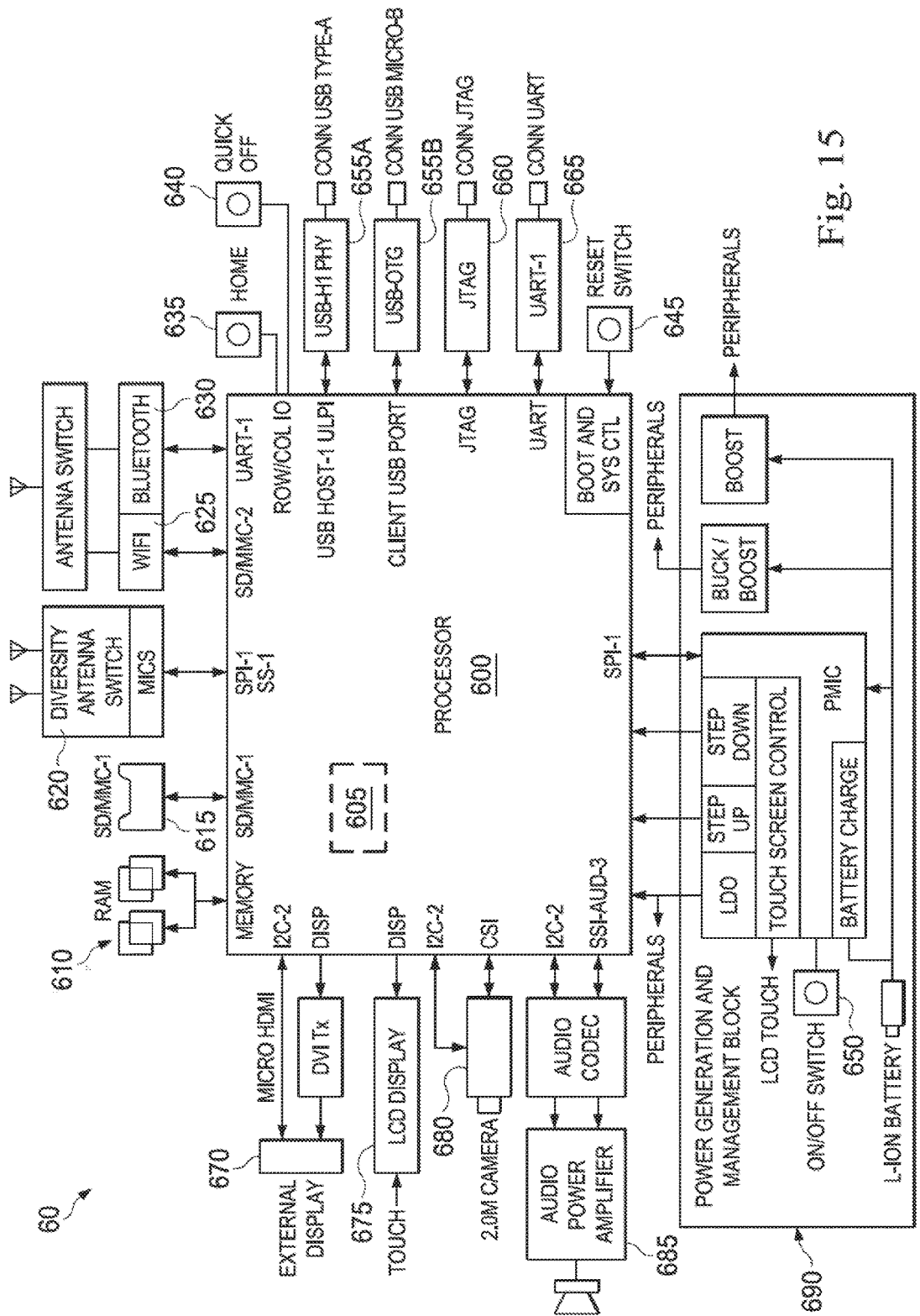
FIG. 15 is a simplified block diagram of an electronic programmer according to various aspects of the present disclosure.

FIG. 15 shows a block diagram of one embodiment of the clinician programmer (CP) 60 (FIG. 1) that can be used to display the visual representations of a medical therapy discussed above. It is understood, however, that alternative embodiments of the CP may be used to perform these representations as well.

The CP includes a printed circuit board ("PCB") that is populated with a plurality of electrical and electronic components that provide power, operational control, and protection to the CP. With reference to FIG. 15, the CP includes a processor 600. The processor 600 controls the CP. In one construction, the processor 600 is an applications processor model i.MX515 available from Freescale Semiconductor®. More specifically, the i.MX515 applications processor has internal instruction and data caches, multimedia capabilities, external memory interfacing, and interfacing flexibility. Further information regarding the i.MX515 applications processor can be found in, for example, the "IMX510EC, Rev. 4" data sheet dated August 2010 and published by Freescale Semiconductor® at www.freescale.com. The content of the data sheet is incorporated herein by reference. Of course, other processing units, such as other microprocessors, microcontrollers, digital signal processors, etc., can be used in place of the processor 600.

The CP includes memory, which can be internal to the processor 600 (e.g., memory 605), external to the processor 600 (e.g., memory 610), or a combination of both. Exemplary memory include a read-only memory ("ROM"), a random access memory ("RAM"), an electrically erasable programmable read-only memory ("EEPROM"), a flash memory, a hard disk, or another suitable magnetic, optical, physical, or electronic memory device. The processor 600 executes software that is capable of being stored in the RAM (e.g., during execution), the ROM (e.g., on a generally permanent basis), or another non-transitory computer readable medium such as another memory or a disc. The CP also includes input/output ("I/O") systems that include routines for transferring information between components within the processor 600 and other components of the CP or external to the CP.

Software included in the implementation of the CP is stored in the memory 605 of the processor 600, RAM 610, ROM 615, or external to the CP. The software includes, for example, firmware, one or more applications, program data, one or more program modules, and other executable instructions. The processor 600 is configured to retrieve from memory and execute, among other things, instructions related to the control processes and methods described below for the CP.

One memory shown in FIG. 15 is memory 610, which may be a double data rate (DDR2) synchronous dynamic random access memory (SDRAM) for storing data relating to and captured during the operation of the CP. In addition, a secure digital (SD) multimedia card (MMC) may be coupled to the CP for transferring data from the CP to the memory card via slot 615. Of course, other types of data storage devices may be used in place of the data storage devices shown in FIG. 15.

The CP includes multiple bi-directional radio communication capabilities. Specific wireless portions included with the CP are a Medical Implant Communication Service (MICS) bi-directional radio communication portion 620, a WiFi bi-directional radio communication portion 625, and a Bluetooth bi-directional radio communication portion 630. The MICS portion 620 includes a MICS communication interface, an antenna switch, and a related antenna, all of which allows wireless communication using the MICS specification. The WiFi portion 625 and Bluetooth portion 630 include a WiFi communication interface, a Bluetooth communication interface, an antenna switch, and a related antenna all of which allows wireless communication following the WiFi Alliance standard and Bluetooth Special Interest Group standard. Of course, other wireless local area network (WLAN) standards and wireless personal area networks (WPAN) standards can be used with the CP.

The CP includes three hard buttons: a "home" button 635 for returning the CP to a home screen for the device, a "quick off" button 640 for quickly deactivating stimulation IPG, and a "reset" button 645 for rebooting the CP. The CP also includes an "ON/OFF" switch 650, which is part of the power generation and management block (discussed below).

The CP includes multiple communication portions for wired communication. Exemplary circuitry and ports for receiving a wired connector include a portion and related port for supporting universal serial bus (USB) connectivity 655, including a Type A port and a Micro-B port; a portion and related port for supporting Joint Test Action Group (JTAG) connectivity 660, and a portion and related port for supporting universal asynchronous receiver/transmitter (UART) connectivity 665. Of course, other wired communication standards and connectivity can be used with or in place of the types shown in FIG. 15.

Another device connectable to the CP, and therefore supported by the CP, is an external display. The connection to the external display can be made via a micro High-Definition Multimedia Interface (HDMI) 670, which provides a compact audio/video interface for transmitting uncompressed digital data to the external display. The use of the HDMI connection 670 allows the CP to transmit video (and audio) communication to an external display. This may be beneficial in situations where others (e.g., the surgeon) may want to view the information being viewed by the healthcare professional. The surgeon typically has no visual access to the CP in the operating room unless an external screen is provided. The HDMI connection 670 allows the surgeon to view information from the CP, thereby allowing greater communication between the clinician and the surgeon. For a specific example, the HDMI connection 670 can broadcast a high definition television signal that allows the surgeon to view the same information that is shown on the LCD (discussed below) of the CP.

The CP includes a touch screen I/O device 675 for providing a user interface with the clinician. The touch screen display 675 can be a liquid crystal display (LCD) having a resistive, capacitive, or similar touch-screen technology. It is envisioned that multitouch capabilities can be used with the touch screen display 675 depending on the type of technology used.

The CP includes a camera 680 allowing the device to take pictures or video. The resulting image files can be used to document a procedure or an aspect of the procedure. Other devices can be coupled to the CP to provide further information, such as scanners or RFID detection. Similarly, the CP includes an audio portion 685 having an audio codec circuit, audio power amplifier, and related speaker for providing audio communication to the user, such as the clinician or the surgeon.

The CP further includes a power generation and management block 690. The power block 690 has a power source (e.g., a lithium-ion battery) and a power supply for providing multiple power voltages to the processor, LCD touch screen, and peripherals.

In one embodiment, the CP is a handheld computing tablet with touch screen capabilities. The tablet is a portable personal computer with a touch screen, which is typically the primary input device. However, an external keyboard or mouse can be attached to the CP. The tablet allows for mobile functionality not associated with even typical laptop personal computers. The hardware may include a Graphical Processing Unit (GPU) in order to speed up the user experience. An Ethernet port (not shown in FIG. 15) may also be included for data transfer.

It is understood that a patient programmer may be implemented in a similar manner as the clinician programmer shown in FIG. 15. Also, according to the present disclosure, the visual representation of the medical therapy discussed above with reference to FIGS. 2-12 may be implemented in an electronic device such as the clinician programmer 60 or a suitable patient programmer. For example, the visual representations may be implemented on the clinician or patient programmers through an appropriate user interface, such as those shown in FIGS. 2-8 discussed above.

Furthermore, though the various visual representation concepts of the present disclosure are explained using an implanted pulse generator (IPG) as an example, it is understood that these concepts may apply to other types of implanted medical devices as well, such as pacemakers, etc.

Figure 16B:
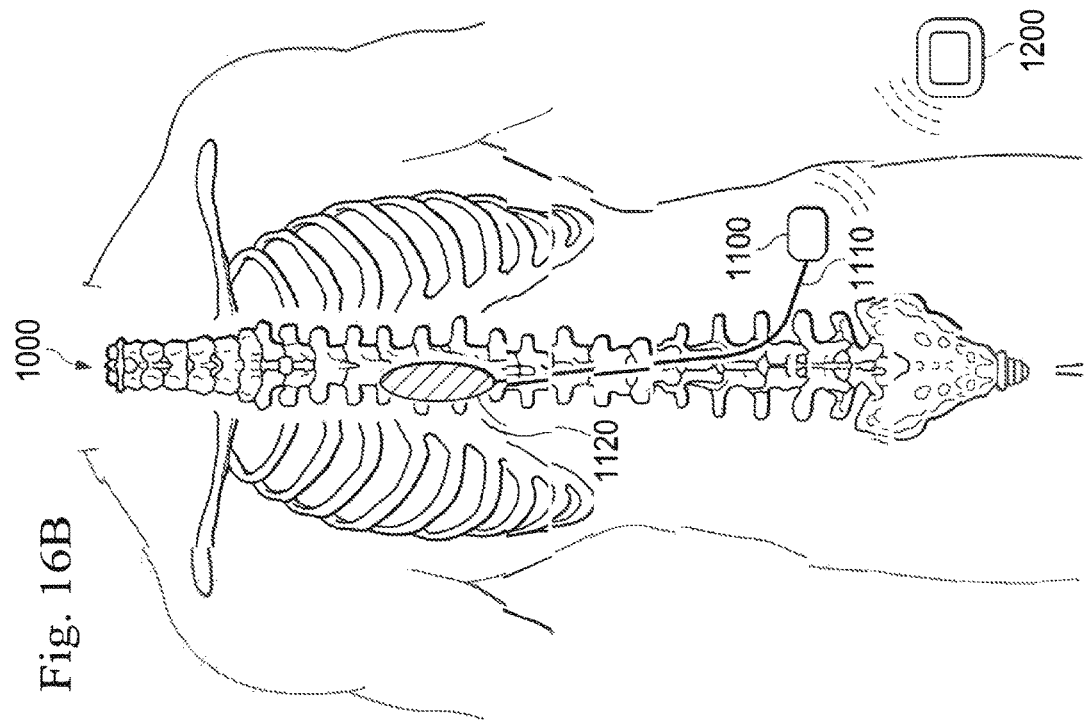
FIGS. 16A and 16B are side and posterior views of a human spine, respectively.
Figure 16A:
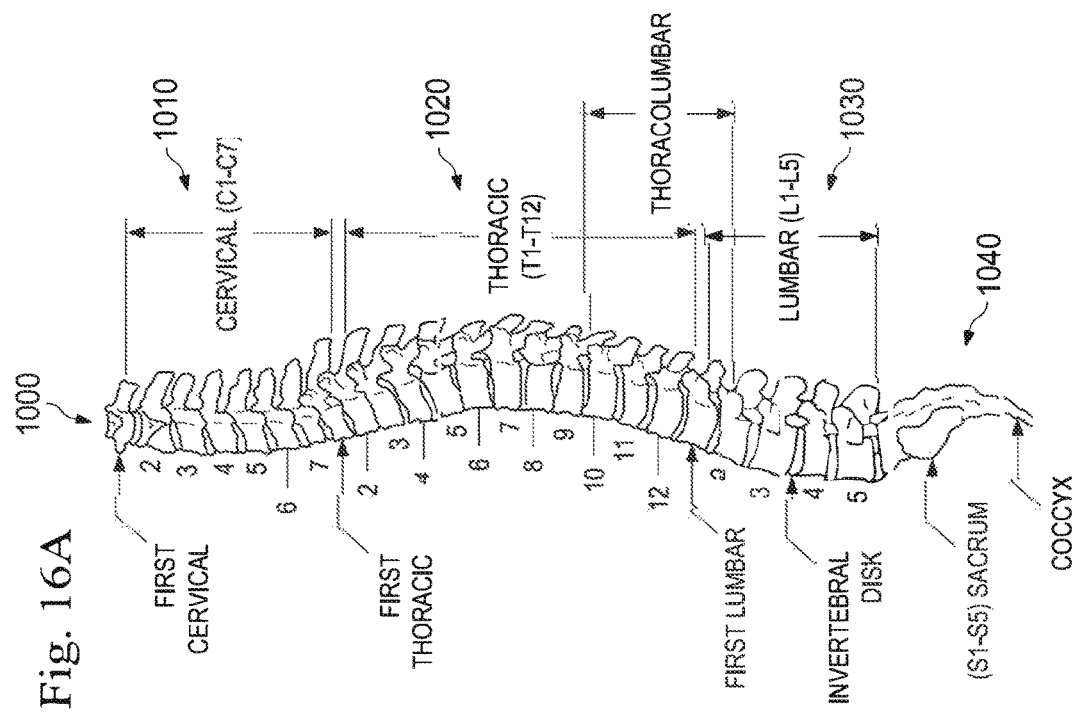

FIG. 16A is a side view of a spine 1000, and FIG. 16B is a posterior view of the spine 1000. The spine 1000 includes a cervical region 1010, a thoracic region 1020, a lumbar region 1030, and a sacrococcygeal region 1040. The cervical region 1010 includes the top 7 vertebrae, which may be designated with C1-C7. The thoracic region 1020 includes the next 12 vertebrae below the cervical region 1010, which may be designated with T1-T12. The lumbar region 1030 includes the final 5 "true" vertebrae, which may be designated with L1-L5. The sacrococcygeal region 1040 includes 9 fused vertebrae that make up the sacrum and the coccyx. The fused vertebrae of the sacrum may be designated with S1-S5.

Neural tissue (not illustrated for the sake of simplicity) branch off from the spinal cord through spaces between the vertebrae. The neural tissue can be individually and selectively stimulated in accordance with various aspects of the present disclosure. For example, referring to FIG. 16B, an IPG device 1100 is implanted inside the body. The IPG device 1100 may include a neurostimulator device. A conductive lead 1110 is electrically coupled to the circuitry inside the IPG device 1100. The conductive lead 1110 may be removably coupled to the IPG device 1100 through a connector, for example. A distal end of the conductive lead 1110 is attached to one or more electrodes 1120. The electrodes 1120 are implanted adjacent to a desired nerve tissue in the thoracic region 1020. Using well-established and known techniques in the art, the distal end of the lead 1110 with its accompanying electrodes may be positioned along or near the epidural space of the spinal cord. It is understood that although only one conductive lead 1110 is shown herein for the sake of simplicity, more than one conductive lead 1110 and corresponding electrodes 1120 may be implanted and connected to the IPG device 1100.

The electrodes 1120 deliver current drawn from the current sources in the IPG device 1100, therefore generating an electric field near the neural tissue. The electric field stimulates the neural tissue to accomplish its intended functions. For example, the neural stimulation may alleviate pain in an embodiment. In other embodiments, a stimulator may be placed in different locations throughout the body and may be programmed to address a variety of problems, including for example but without limitation; prevention or reduction of epileptic seizures, weight control or regulation of heart beats.

It is understood that the IPG device 1100, the lead 1110, and the electrodes 1120 may be implanted completely inside the body, may be positioned completely outside the body or may have only one or more components implanted within the body while other components remain outside the body. When they are implanted inside the body, the implant location may be adjusted (e.g., anywhere along the spine 1000) to deliver the intended therapeutic effects of spinal cord electrical stimulation in a desired region of the spine. Furthermore, it is understood that the IPG device 1100 may be controlled by a patient programmer or a clinician programmer 1200, the implementation of which may be similar to the clinician programmer shown in FIG. 15.

The foregoing has outlined features of several embodiments so that those skilled in the art may better understand the detailed description that follows. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions and alterations herein without departing from the spirit and scope of the present disclosure.

What is claimed is:

1. A method of visualizing medical therapy associated with an implantable medical device, the method comprising:
    providing a first level user interface for a stimulation program that can be executed on the implantable medical device to provide electrical stimulation for a patient as a part of the medical therapy, wherein the first level user interface is configured to display, and allow an adjustment of, a plurality of stimulation parameters of the stimulation program;
    providing a second level user interface for a stimulation program-set that is a collection of different stimulation programs, wherein the second level user interface is configured to display a plurality of visual abstractions that each correspond to a respective one of the stimulation programs, and wherein each visual abstraction of the stimulation program displays at least one of the stimulation parameters associated with the respective stimulation program; and providing a third level user interface for a stimulation program-set list that is a collection of different stimulation program-sets, wherein the third level user interface is configured to display a scrollable virtual carousel made up of a plurality of visual abstractions that each correspond to a respective one of the stimulation program-sets, and wherein each visual abstraction of the stimulation program-set displays at least one of: a patient-defined stimulation map and a patient-defined pain map.

2. The method of claim 1, further comprising: displaying the first level user interface, second level user interface, and third level user interface one at a time on a touchscreen device.

3. The method of claim 1, wherein the first level user interface is further configured to display a virtual representation of the implantable medical device and its target anatomical environment.

4. The method of claim 1, wherein the second level user interface is further configured to display a stimulation parameter that is common to all of the stimulation programs within the stimulation program-set.

5. The method of claim 1, wherein the third level user interface is further configured to display, on each visual abstraction of the stimulation program-set, a stimulation parameter that is common to all of the stimulation programs within the stimulation program-set.

6. The method of claim 1, further comprising: generating the patient-defined stimulation map or the patient-defined pain map in response to patient input, wherein boundaries of the stimulation map and the pain map are customizable.

7. The method of claim 1, further comprising:
selecting a target stimulation program-set for execution;
executing each of the stimulation programs in the stimulation program-set; and
repeating the executing.

8. The method of claim 1, further comprising: denying an access of the first level user interface by the patient.

9. The method of claim 1, wherein the first level user interface, the second level user interface, and the third level user interface are each implemented on a portable electronic device that is one of: a clinician programmer, a patient programmer, and a computer tablet.

10. The method of claim 1, further comprising: navigating between the first level user interface, the second level user interface, and the third level user interface in response to a user engagement of one or more virtual mechanisms displayed as a part of the first level user interface, the second level user interface, and the third level user interface.

11. A method of visualizing medical therapy associated with an implantable medical device, the method comprising:
displaying, via a first screen of a graphical user interface, a visual representation of a stimulation program that can be executed on the implantable medical device to provide electrical stimulation for a patient as a part of the medical therapy, wherein the visual representation of the stimulation program includes one or more stimulation parameters;
displaying, via a second screen of the graphical user interface, a visual representation of a stimulation program-set that is a collection of different stimulation programs; and
displaying, via a third screen of the graphical user interface, a visual representation of a stimulation program-set list that is a collection of different stimulation program-sets.

12. The method of claim 11, further comprising:
navigating between the first screen and the second screen in response to a user engagement of a first virtual mechanism displayed in the first screen or the second screen; and
navigating between the second screen and the third screen in response to a user engagement of a second virtual mechanism displayed in the second screen or the third screen;
wherein the user includes a healthcare professional but does not include a patient.

13. The method of claim 11, wherein the displaying the visual representation of the stimulation program comprises displaying a plurality of user-adjustable values of a plurality of stimulation parameters via the first screen.

14. The method of claim 13, wherein the first screen further includes a virtual representation of the implantable medical device and a target anatomical environment of the implantable medical device in a human body model.

15. The method of claim 11, wherein the displaying the visual representation of the stimulation program-set comprises displaying a plurality of first visual elements that each correspond to a different one of the stimulation programs via the second screen, and wherein the first visual elements each contain a summary of values of the stimulation parameters used for the corresponding stimulation program.

16. The method of claim 11, wherein the displaying the visual representation of the stimulation program-set list comprises displaying a plurality of second visual elements that each correspond to a different one of the stimulation program-sets via the third screen, and wherein the second visual elements each visually illustrate, on a human body model, a pain map or a stimulation map associated with the corresponding stimulation program-set.

17. The method of claim 16, wherein the second visual elements are displayed as a scrollable carousel.

18. The method of claim 11, further comprising:
selecting a target stimulation program-set for execution; and
automatically executing, in response to the selecting and without needing additional user input, each of the stimulation programs in the stimulation program-set.

19. A method of visualizing medical therapy associated with an implantable medical device, the method comprising:
displaying, via a first screen of a graphical user interface, a visual representation of a stimulation program that can be executed on the implantable medical device to provide electrical stimulation for a patient as a part of the medical therapy, wherein the visual representation of the stimulation program includes a plurality of user-adjustable stimulation parameters;
displaying, via a second screen of the graphical user interface, a visual representation of a stimulation program-set that includes of different stimulation programs, wherein the visual representation of the stimulation program-set includes a plurality of first visual elements that each contain a summary of values of the stimulation parameters used for the corresponding stimulation program; and
displaying, via a third screen of the graphical user interface, a visual representation of a stimulation program-set list that is a collection of different stimulation program-sets, wherein the visual representation of the stimulation program-set list includes a plurality of second visual elements that each visually illustrate, on a human body model, a pain map or a stimulation map associated with the corresponding stimulation program-set.

20. The method of claim 19, further comprising: automatically and repeatedly executing, in response to a user selection of a target stimulation program-set, each of the stimulation programs in the stimulation program-set.

\* \* \* \* \*